(12) United States Patent
Deng et al.

(10) Patent No.: US 9,902,715 B2
(45) Date of Patent: Feb. 27, 2018

(54) COMPOUNDS

(71) Applicant: GLAXOSMITHKLINE INTELLECTUAL PROPERTY DEVELOPMENT LIMITED, Middlesex (GB)

(72) Inventors: Jing Deng, Shanghai (CN); Hui Lei, Shanghai (CN); Xin Ma, Shanghai (CN); Feng Ren, Shanghai (CN); Wei Cai, Shanghai (CN); Xichen Lin, Shanghai (CN)

(73) Assignee: GLAXOSMITHKLINE INTELLECTUAL PROPERTY DEVELOPMENT LIMITED, Brentford, Middlesex (GB)

( * ) Notice: Subject to any disclaimer, the term of this patent is extended or adjusted under 35 U.S.C. 154(b) by 0 days.

(21) Appl. No.: 15/314,106

(22) PCT Filed: May 26, 2015

(86) PCT No.: PCT/CN2015/079754
§ 371 (c)(1),
(2) Date: Nov. 28, 2016

(87) PCT Pub. No.: WO2015/180613
PCT Pub. Date: Dec. 3, 2015

(65) Prior Publication Data
US 2017/0121313 A1    May 4, 2017

(30) Foreign Application Priority Data
May 28, 2014   (WO) ................ PCT/CN2014/078699

(51) Int. Cl.
*C07D 403/12*  (2006.01)
*C07D 403/06*  (2006.01)
*C07D 401/12*  (2006.01)
*C07D 403/14*  (2006.01)
*C07D 401/06*  (2006.01)
*C07D 401/14*  (2006.01)
*C07D 241/04*  (2006.01)

(52) U.S. Cl.
CPC ......... *C07D 403/14* (2013.01); *C07D 241/04* (2013.01); *C07D 401/06* (2013.01); *C07D 401/12* (2013.01); *C07D 401/14* (2013.01); *C07D 403/06* (2013.01); *C07D 403/12* (2013.01)

(58) Field of Classification Search
CPC .. C07D 403/14; C07D 403/06; C07D 403/12; C07D 401/12; C07D 401/14; C07D 401/06; C07D 241/04
See application file for complete search history.

(56) References Cited

U.S. PATENT DOCUMENTS

| 8,604,069 | B2 | 12/2013 | Maeba et al. |
| 9,150,508 | B2 | 10/2015 | Birault et al. |
| 9,242,972 | B2 | 1/2016 | Birault et al. |
| 9,428,452 | B2 | 8/2016 | Birault et al. |
| 9,540,318 | B2 | 1/2017 | Birault et al. |
| 2015/0299121 | A1 | 10/2015 | Han et al. |
| 2016/0257664 | A1 | 9/2016 | Birault et al. |
| 2016/0304478 | A1 | 10/2016 | Birault et al. |
| 2017/0081278 | A1 | 3/2017 | Birault et al. |
| 2017/0101399 | A1 | 4/2017 | Lei et al. |
| 2017/0197978 | A1 | 7/2017 | Deng et al. |

FOREIGN PATENT DOCUMENTS

| WO | WO 2007/022257 A2 | 2/2007 | |
| WO | WO 2007/070626 A2 | 6/2007 | |
| WO | WO 2007/078839 A2 | 7/2007 | |
| WO | WO 2007/089336 A2 | 8/2007 | |
| WO | WO 2012/027965 A1 | 3/2012 | |
| WO | WO 2012/028100 A1 | 3/2012 | |
| WO | WO 2012/100732 A1 | 8/2012 | |
| WO | WO 2012/100734 A1 | 8/2012 | |
| WO | WO 2012/145254 A2 | 10/2012 | |
| WO | WO 2012139775 A1 | 10/2012 | |
| WO | WO 2012/147916 A1 | 11/2012 | |
| WO | WO 2012/158784 | * 11/2012 | ......... A61K 31/5375 |
| WO | WO 2012158784 A2 | 11/2012 | |
| WO | WO 2013/036912 A2 | 3/2013 | |
| WO | WO 2013/045431 A1 | 4/2013 | |
| WO | WO 2013/160418 A1 | 10/2013 | |
| WO | WO 2013/160419 A1 | 10/2013 | |
| WO | WO 2013/171729 A2 | 11/2013 | |
| WO | WO 2014/086894 A1 | 6/2014 | |
| WO | WO 2015/061515 A1 | 4/2015 | |
| WO | WO 2015/061686 A2 | 4/2015 | |
| WO | WO 2015/180612 A1 | 12/2015 | |
| WO | WO 2015/180614 A1 | 12/2015 | |

OTHER PUBLICATIONS

Leipe, et al. Arthritis & Rheumatism, 62(10): 2876-2885 (Oct. 2010).
Rutz, et al. Cytokine & Growth Factor Reviews, 30: 1-17 (2016).
Xue, et al. Scientific Reports, 1-17 (2016). Available online at www.nature.com/scientificreports/.
Silverman. The Organic Chemistry of Drug Design and Action, 25-34 (2004).

\* cited by examiner

*Primary Examiner* — Erich A Leeser
(74) *Attorney, Agent, or Firm* — Dara L. Dinner; Edward R. Gimmi; William R. Majarian

(57) ABSTRACT

The present invention relates to novel retinoid-related orphan receptor gamma (RORγ) modulators and their use in the treatment of diseases mediated by RORγ.

21 Claims, No Drawings

COMPOUNDS

This application is a 371 of International Application No. PCT/CN2015/079754, filed 26 May 2015, claims benefit to PCT Application PCT/CN2014/078699 filed 28 May 2014.

The present invention relates to novel retinoid-related orphan receptor gamma (RORγ) modulators and their use in the treatment of diseases mediated by RORγ.

BACKGROUND OF THE INVENTION

Retinoid-related orphan receptors (RORs) are transcription factors which belong to the steroid hormone nuclear receptor superfamily (Jetten & Joo (2006) *Adv. Dev. Biol.* 16:313-355). The ROR family consists of three members, ROR alpha (RORα), ROR beta (RORβ) and ROR gamma (RORγ), each encoded by a separate gene (RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal NB domain. Two isoforms of RORγ have been identified: ROR-γ1 and RORγt (also known as RORγ2). RORγ is a term used to describe both RORγ1 and/or RORγt.

While RORγ1 is expressed in a variety of tissues including thymus, muscle, kidney and liver, RORγt is exclusively expressed in the cells of the immune system. RORγt has been identified as a key regulator of Th17 cell differentiation. Th17 cells are a subset of T helper cells which produce IL-17 and other proinflammatory cytokines. Th17 cells have been shown to have key functions in several mouse autoimmune disease models including experimental autoimmune encephalomyelitis (EAE) and collagen-induced arthritis (CIA). In addition, Th17 cells or their products have been shown to be associated with the pathology of a variety of human inflammatory and autoimmune disorders including multiple sclerosis, rheumatoid arthritis, psoriasis, ankylosing spondylitis, Crohn's disease and asthma (Jetten (2009) *Nucl. Recept. Signal.* 7: e003; Manel et al. (2008) *Nat. Immunol.* 9:641-649; Miossec & Kolls (2012) *Nat. Rev. Drug. Discov.* 10:763-776). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman (2008) *J. Exp. Med.* 205:1517-1522; Leung et al. (2010) *Cell. Mol. Immunol.* 7:182-189). There is evidence that Th17 cells are activated during the disease process and are responsible for recruiting other inflammatory cells types, especially neutrophils, to mediate pathology in the target tissues (Korn et al. (2009) *Annu. Rev. Immunol.* 27:485-517).

RORγt plays a critical role in the pathogenic responses of Th17 cells (Ivanov et al. (2006) *Cell* 126:1121-1133). RORγt deficient mice show very little Th17 cells. In addition, RORγt deficiency resulted in amelioration of EAE. Further support for the role of RORγt in the pathogensis of autoimmune or inflammatory diseases can be found in the following references: Jetten & Joo (2006) *Adv. Dev. Biol.* 16:313-355; Meier et al. (2007) *Immunity* 26:643-654; Aloisi & Pujol-Borrell (2006) *Nat. Rev. Immunol.* 6:205-217; Jager et al. (2009) *J. Immunol.* 183:7169-7177; Serafini et al. (2004) *Brain Pathol.* 14:164-174; Magliozzi et al. (2007) *Brain* 130:1089-1104; Barnes (2008) *Nat. Rev. Immunol.* 8:183-192; Miossec & Kolls (2012) *Nat. Rev. Drug. Discov.* 10:763-776.

In light of the role RORγ plays in the pathogenesis of diseases, it is desirable to prepare compounds that modulate RORγ activity, which can be used in the treatment of diseases mediated by RORγ.

SUMMARY OF THE INVENTION

The invention is directed to novel RORγ modulators and their use in the treatment of diseases mediated by RORγ. Specifically, the invention is directed to compounds according to Formula I.

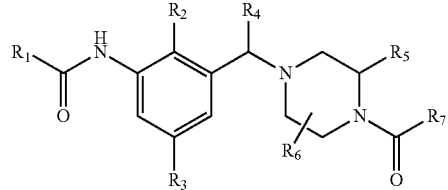

Formula I wherein $R_1$ to $R_7$ are defined below, and to pharmaceutically-acceptable salts thereof.

In another aspect, this invention provides for the use of the compounds of Formula (I) for the treatment of diseases mediated by RORγ. Examples of such diseases include autoimmune or inflammatory diseases such as multiple sclerosis, rheumatoid arthritis, psoriasis and ankylosing spondylitis. In yet another aspect, the invention is directed to methods of treating such diseases.

DETAILED DESCRIPTION OF THE INVENTION

Terms and Definitions

"Alkyl" refers to a monovalent saturated hydrocarbon chain having the specified number of member atoms. For example, C1-C6 alkyl refers to an alkyl group having from 1 to 6 member atoms. Alkyl groups may be optionally substituted with one or more substituent as defined herein. Alkyl groups may be straight or branched. Representative branched alkyl groups have one, two, or three branches. Examples of alkyl include methyl, ethyl, propyl (n-propyl and isopropyl), butyl (n-butyl, isobutyl, and t-butyl), pentyl (n-pentyl, isopentyl, and neopentyl), and hexyl.

"Cycloalkyl" refers to a saturated hydrocarbon ring having the specified number of member atoms. Cycloalkyl groups are monocyclic ring systems or are fused or bridged bicyclic ring systems. For example, C3-C7 cycloalkyl refers to a cycloalkyl group having from 3 to 7 member atoms. Cycloalkyl groups may be optionally substituted with one or more substituent as defined herein. Examples of cycloalkyl include cyclopropyl, cyclobutyl, cyclopentyl, and cyclohexyl.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct species in vitro or in vivo.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems or are fused or bridged bicyclic ring systems. Monocyclic heteroaryl rings have from 5 to 7 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Examples of heteroaryl include pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, furopyridinyl, and naphthyridinyl.

"Heteroatom" refers to a nitrogen, sulphur, or oxygen atom.

"Heterocycloalkyl" refers to a saturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups are monocyclic ring systems or are fused, spiro, or bridged bicyclic ring systems. Monocyclic heterocycloalkyl rings have from 4 to 7 member atoms. Bicyclic heterocycloalkyl rings have from 7 to 11 member atoms. Examples of heterocycloalkyl include pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,3-oxathiolanyl, 1,3-dithianyl, azetidinyl, oxetanyl, azabicylo[3.2.1]octyl, and oxabicylo[2.2.1]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituent as defined.

"RORγ" refers to all isoforms encoded by the RORC gene which include RORγ1 and RORγt.

"RORγ modulator" refers to a chemical compound that inhibits, either directly or indirectly, the activity of RORγ. RORγ modulators include antagonists and inverse agonists of RORγ.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom.

Compounds

The present invention provides a compound of Formula I or a pharmaceutically acceptable salt thereof.

Formula I

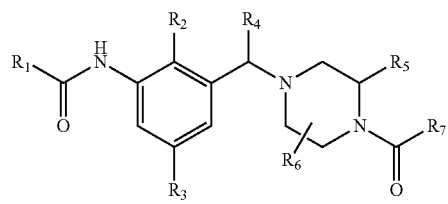

wherein:
R1 is:
  methyl substituted with i) C4-C6 cycloalkyl optionally substituted with a) one or two F or b) OH; or ii) 5 or 6 membered heterocycloalkyl substituted with C(O)CH₃;
  C2-C3 alkyl substituted with CF₃ or —SO₂CH₃;
  6 membered heteroaryl containing 1 or 2 N atom, said heteroaryl is optionally substituted with one to two substituents selected from the group consisting of: C1-C3 alkyl, halo, CN and methoxy; or
  phenyl substituted with CN;
R2 is C1-C3 alkyl;
R3 is halo or CN;
R4 is H;
R5 is C1-C3 alkyl;
R6 is H or methyl; and
R7 is selected from the group consisting of:
  4 to 6 membered heterocycloalkyl containing 1 N atom, wherein said heterocycloalkyl is optionally substituted with methyl;
  NRaRb, wherein said Ra is H or methyl, and said Rb is selected from the group consisting of i) methyl substituted with C3-C4 cycloalkyl; ii) C4-C5 cycloalkyl optionally substituted with methyl; and iii) C3-C4 alkyl; and ORc, wherein said Rc is i) C4-C5 cycloalkyl or ii) methyl substituted with C3-C4 cycloalkyl.

In one embodiment, the invention relates to the compounds of Formula I, wherein R1 is 6 membered heteroaryl containing 1 or 2 N atoms, wherein said heteroaryl is substituted with one or two C1-C3 alkyl. In one embodiment, this invention also relates to compounds of any of the above embodiments, wherein R1 is pyridinyl substituted with methyl. In one embodiment, this invention also relates to compounds of any of the above embodiments, wherein R1 is pyridinyl substituted with dimethyl.

In one embodiment, the invention relates to the compounds of Formula I, wherein R1 is phenyl substituted with CN.

In one embodiment, this invention also relates to compounds of any of the above embodiments, wherein R2 is C1-C3 alkyl. In one embodiment, this invention also relates to compounds of any of the above embodiments, wherein R2 is methyl.

In one embodiment, this invention also relates to compounds of any of the above embodiments, wherein R3 is halo. In one embodiment, this invention also relates to compounds of any of the above embodiments, wherein R3 is Cl.

In one embodiment, this invention also relates to compounds of any of the above embodiments, wherein R3 is CN.

In one embodiment, this invention also relates to compounds of any of the above embodiments, wherein R4 is H.

In one embodiment, this invention also relates to compounds of any of the above embodiments, wherein R5 is methyl.

In one embodiment, this invention also relates to compounds of any of the above embodiments, wherein R6 is H.

In one embodiment, this invention also relates to compounds of any of the above embodiments, wherein R7 is 4 to 6 membered heterocycloalkyl containing 1 N atom. In one embodiment, this invention also relates to compounds of any of the above embodiments, wherein R7 is pyrrolidinyl. In one embodiment, this invention also relates to compounds of any of the above embodiments, wherein R7 is piperidinyl.

In one embodiment, this invention also relates to compounds of any of the above embodiments, wherein R7 is ORc, wherein Rc is cyclopentyl.

In one embodiment, this invention also relates to compounds of any of the above embodiments, wherein R7 is NHRb and Rb is methyl substituted with cyclopropyl. In one embodiment, this invention also relates to compounds of any of the above embodiments, wherein R7 is NHRb and Rb is cyclopentyl.

In one embodiment, the invention relates to compounds of Formula (I), wherein R1 is pyridinyl substituted with one or two methyl, R2 is methyl, R3 is Cl, R4 is H, R5 is methyl, R6 is H, and R7 is NHRb, wherein Rb is i) cyclopentyl or ii) methyl substituted with cyclopropyl.

In one embodiment, the invention relates to compounds of Formula (I), wherein R1 is pyridinyl substituted With methyl, R2 is methyl, R3 is Cl, R4 is H, R5 is methyl, R6 is H, and R7 is piperidinyl;

In another embodiment, the invention relates to compounds of Formula (I), wherein R1 is phenyl substituted with CN, R2 is methyl, R3 is Cl, R4 is H, R5 is methyl, R6 is H, and R7 is i) pyrrolidinyl or ii) NHRb, wherein Rb is methyl substituted with cyclopropyl.

In yet another embodiment, the invention relates to compounds of Formula (I), wherein R1 is pyridinyl substituted with methyl, R2 is methyl, R3 is Cl, R4 is H, R5 is methyl, R6 is H, and R7 is ORc, wherein Rc is cyclopentyl.

In one embodiment, the compound of Formula I is selected from:

(S)-4-(5-chloro-3-(5,6-dimethylnicotinamido)-2-methylbenzyl)-N-(cyclopropylmethyl)-2-methylpiperazine-1-carboxamide (E1);

(S)-4-(5-chloro-3-(3-cyanobenzamido)-2-methylbenzyl)-N-(cyclopropylmethyl)-2-methylpiperazine-1-carboxamide, trifluoroacetic acid salt (E24);

(S)-N-(5-chloro-2-methyl-3-((3-methyl-4-(pyrrolidine-1-carbonyl)piperazin-1-yl)methyl)phenyl)-3-cyanobenzamide (E25);

(S)-4-(5-chloro-2-methyl-3-(6-methylnicotinamido)benzyl)-N-cyclopentyl-2-methylpiperazine-1-carboxamide (E29);

(S)-N-(5-chloro-2-methyl-3-((3-methyl-4-(piperidine-1-carbonyl)piperazin-1-yl)methyl)phenyl)-6-methylnicotinamide (30);

(S)-cyclopentyl 4-(5-cyano-2-methyl-3-(6-methylnicotinamido)benzyl)-2-methylpiperazine-1-carboxylate (E44).

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzamatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may contain an acidic functional group. In certain other embodiments, compounds according to Formula I may contain a basic functional group. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts may impart greater stability or solubility to the molecule thereby facilitating formulation into a dosage form. Accordingly, the invention is further directed to the use of pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively. Suitable pharmaceutically acceptable salts include those described by Berge, Bighley, and Monlchouse, *J. Pharm. Sci.* (1977) 66, pp 1-19.

Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing an acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glutamine, N-methylglucamine, collidine, choline, quinine, quinoline, and basic amino acid such as lysine and arginine.

Other salts, which are not pharmaceutically acceptable, may be useful in the preparation of compounds of this invention and these should be considered to form a further aspect of the invention. These salts, such as trifluoroacetate, while not in themselves pharmaceutically acceptable, may be useful in the preparation of salts useful as intermediates in obtaining the compounds of the invention and their pharmaceutically acceptable salts.

If a compound of the invention containing a basic amine or other basic functional group is isolated as a salt, the corresponding free base form of that compound may be prepared by any suitable method known to the art, including treatment of the salt with an inorganic or organic base, suitably an inorganic or organic base having a higher $pK_a$ than the free base form of the compound. Similarly, if a compound of the invention containing an acidic functional group is isolated as a salt, the corresponding free acid form of that compound may be prepared by any suitable method known to the art, including treatment of the salt with an inorganic or organic acid, suitably an inorganic or organic acid having a lower $pK_a$ than the free acid form of the compound.

As used herein, the term "compounds of the invention" means both the compounds according to Formula I and the pharmaceutically-acceptable salts thereof. The term "a compound of the invention" also appears herein and refers to both a compound according to Formula I and its pharmaceutically-acceptable salts.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). Commercially available deuterated starting materials may be employed in the preparation of deuterated forms of the compounds of Formula (I), or they may be synthesized using conventional techniques employing deuterated reagents (e.g. lithium aluminum deuteride).

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing vaiable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compounds of Formula I and pharmaceutically acceptable salts thereof may be employed alone or in combination with other therapeutic agents. Combination therapies according to the present invention thus comprise the administration of at least one compound of Formula I or a pharmaceutically acceptable salt thereof, and the use of at least one other therapeutically active agent. A compound of Formula I or pharmaceutically acceptable salt thereof, and the other therapeutically active agent(s) may be administered together in a single pharmaceutical composition or separately and, when administered separately this may occur simultaneously or sequentially in any order.

In a further aspect, there is provided a combination product comprising a compound of Formula I or a pharmaceutically acceptable salt thereof, together with one or more other therapeutically active agents, and optionally a pharmaceutically acceptable carrier or excipient.

Suitable other therapeutic agents include, but are not limited to, (1) TNF-alpha inhibitors; (2) non-selective COX-1/COX-2 inhibitors; (3) COX-2 inhibitors; (4) other agents for treatment of inflammatory and autoimmune diseases including glucocorticoids, methotrexate, leflunomide, sulfasalazine, azathioprine, cyclosporin, tacrolimus, penicillamine, bucillamine, actarit, mizoribine, lobenzarit, ciclesonide, hydroxychloroquine, d-penicillamine, aurothiomalate, auranofin or parenteral or oral gold, cyclophosphamide, Lymphostat-B, BAFF/APRIL inhibitors, such as belimumab, and CTLA-4-Ig or mimetics thereof; (5) leukotriene biosynthesis inhibitor, 5-lipoxygenase (5-LO) inhibitor or 5-lipoxygenase activating protein (FLAP) antagonist; (6) LTD4 receptor antagonist; (7) PDE4 inhibitor; (8) antihistamine H1 receptor antagonists; (9) a1- and a2-adrenoceptor agonist; (10) anticholinergic agents; (11) (β-adrenoceptor agonists; (12) insulin-like growth factor type I (IGF-1) mimetic; (13) glucocorticosteroids; (14) kinase inhibitors such as inhibitors of the Janus Kinases (JAK 1 and/or JAK2 and/or JAK 3 and/or TYK2), p38 MAPK and IKK2; (15) B-cell targeting biologies such as rituximab; (16) selective costimulation modulators such as abatacept; (17) interleukin inhibitors, such as IL-1 inhibitor anakinra, IL-6 inhibitors tocilizumab or sirukurnab, IL-12/IL-23 inhibitor ustckinumab, IL-23 inhibitor guselkumab, and anti-IL17 antibodies; (18) anti-GM-CSF antibodies; (19) checkpoint blockade and other immunotherapies, such ac anti-PD 1/anti PD-L1 antibodies, including pembrolizumab and nivolumab, and anti-CTLA4 antibodies, including ipilimumab; (20) BET inhibitors, such as GSK525762; and (21) other oncology agents, such as fluorouracil, bevacizumab, irinotecan hydrochloride, capecitabine, cetuximab, ramucirumab, oxaliplatin, leucovorin calcium, panitumumab, regorafenib, ziv-aflibercept, trastuzumab, imatinib mesylate, sunitinib malate, sorafenib tosylate, paclitaxel, everolimus, erlotinib hydrochloride, gemcitabine hydrochloride, mitomycin C, dabrafenib, trametinib, lapatinib, ofatumumab, topotecan, doxorubicin hydrochloride, and ibrutinib.

Compound Preparation

The compounds according to Formula I may be prepared using conventional organic syntheses. Suitable synthetic routes are depicted below in the following general reaction scheme.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

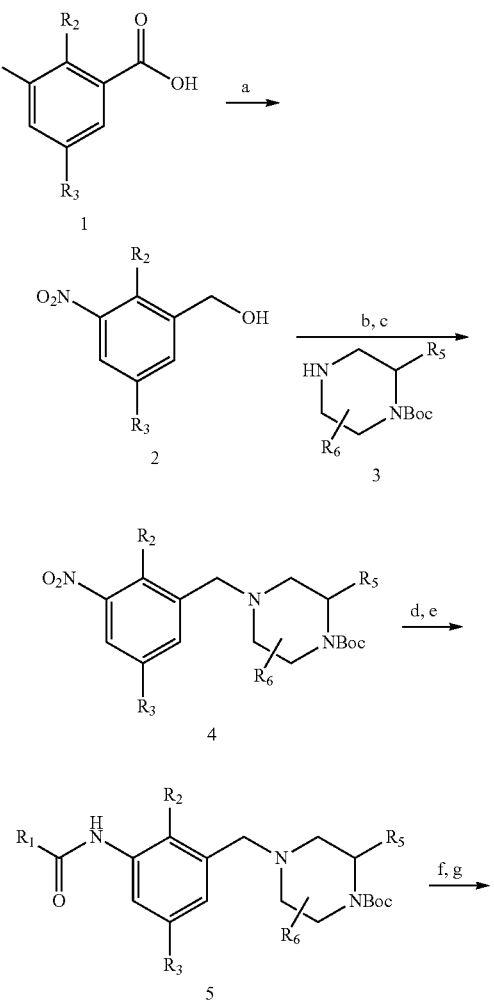

Scheme 1

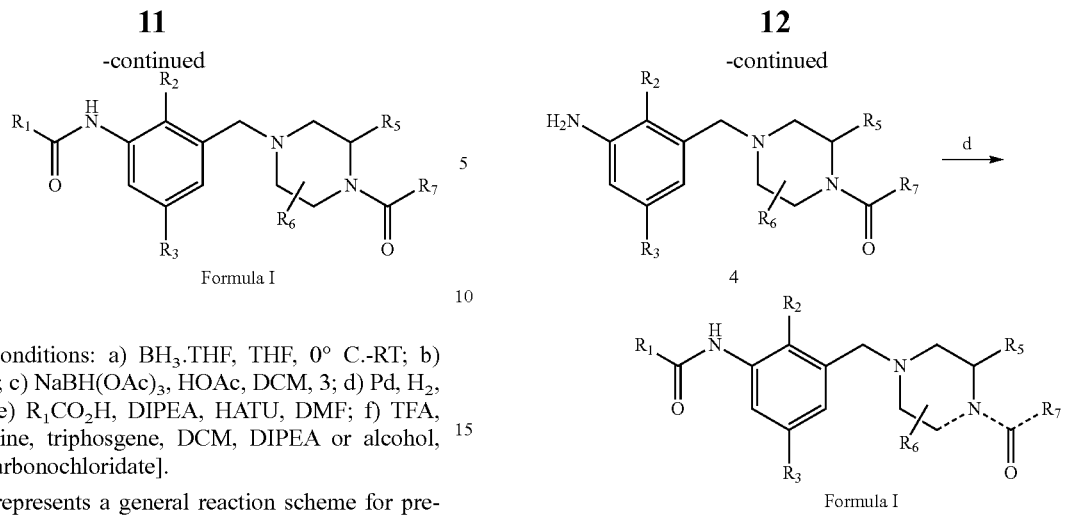

[Exemplary conditions: a) BH₃.THF, THF, 0° C.-RT; b) PCC, CH₂Cl₂; c) NaBH(OAc)₃, HOAc, DCM, 3; d) Pd, H₂, ethanol, RT; e) R₁CO₂H, DIPEA, HATU, DMF; f) TFA, DCM; g) amine, triphosgene, DCM, DIPEA or alcohol, TEA, THF, carbonochloridate].

Scheme 1 represents a general reaction scheme for preparing compounds of Formula I where R1 to R7 are as defined above. The starting material or reagents described are either commercially available or made from commercially available starting materials using methods known to those skilled in the art.

Benzoic acids 1 was reduced by BH₃.THF to provide benzyl alcohols 2. Alcohols 2 were oxidized by PCC to corresponding aldehydes followed by reductive amination with 3 to provide nitro compounds 4. Reduction of nitro compounds 4 with Pd in the presence of H₂ afforded the amines which were reacted with various acids to give amides 5. The Boc protection of 5 was removed by treatment with TFA and the resulting amines reacted with various amines or alcohols to provide final compounds of Formula I.

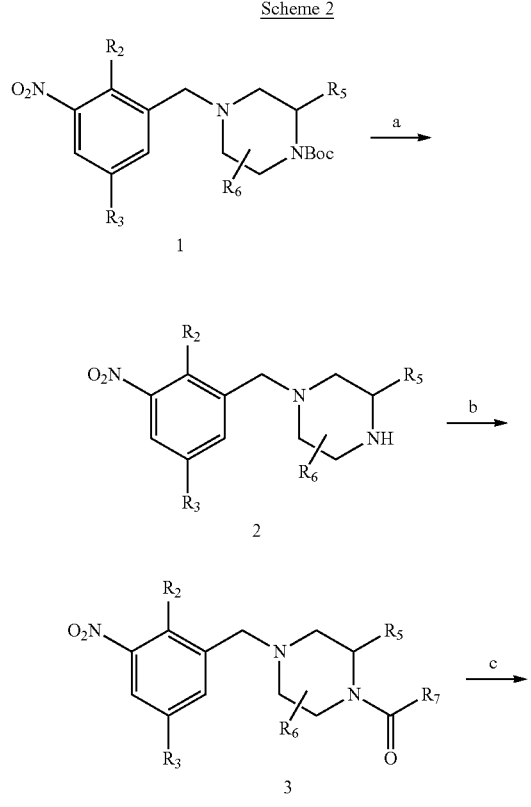

Scheme 2

[Exemplary conditions: a) TFA, DCM, RT; b) amine, triphosgene, THF, 0° C. or alcohol, TEA, THF, carbonochloridates, RT; c) SnCl₂.2H₂O, ethanol, RT; d) R₁CO₂H, HATU, DIPEA, DMF, 50° C.].

Scheme 2 represents another reaction scheme for preparing compounds of Formula I where R1 to R7 are as defined above. The starting material or reagents described are either commercially available or made from commercially available starting materials using methods known to those skilled in the art.

Boc protection on nitro compounds 1 was removed by TFA to provide nitro amines 2, which could then be reacted with various amines or alcohols to give the corresponding ureas or carboxylates 3. The nitro group was reduced to amine by tin(II) chloride dehydrate to afford the key intermediates 4 which were then condensed with various acids to afford final compounds of Formula I.

EXAMPLES

Abbreviations
DCE 1,2-dichloroethane
DCM dichloromethane
DIPEA N,N-diisopropylethylamine
DMAP N,N-dimethylpyridin-4-amine
DMF N,N-dimethylformamide
DMSO dimethylsulphoxide
EA ethyl acetate
EDC  N-(3-dimethylaminopropyl)-N'-ethylcarbodiimide hydrochloride
ESI electrospray ionization
HATU O-(7-azabenzotriazol-1-yl)-N,N,N',N'-tetramethyluronium hexafluorophosphate
HOBt Hydroxybenzotriazole
HPLC high-performance liquid chromatography
LCMS liquid chromatography mass spectrometry
MS mass spectrometry
NBS n-bromosuccinamide
NMP N-methyl-2-pyrrolidone
PE petroleum ether
PCC pyridinium chlorochromate
PG protecting group
RT room temperature
sat. saturated
TEA triethylamine
TFA trifluoroacetic acid
THF tetrahydrofuran Chromatography Unless stated otherwise, all chromatography was carried out using silica columns.

LCMS Conditions:
1) Acidic conditions:
   Mobile phase: water containing 0.05% TFA/acetonitrile
   Column: Agilent SB-C18 4.6×30 mm 1.8 m
   Detection: MS and photodiode array detector (PDA)
2) Basic Conditions:
   Mobile phase: 10 mM $NH_4HCO_3$ aqueous/acetonitrile
   Column: Waters XBridge C18 4.6×50 mm 3.5 m
   Detection: MS and photodiode array detector (PDA)

HPLC Conditions:
1) Instrument:
   PHG016
   Gilson 281
   Waters
2) Column:
   Xbridge Prep C18 10 μm OBD, 19×250 mm
   Boston, pHlex ODS, 21.2×250 mm, 10 μm, 100 A
   Shimadzu Shim-Pack, PRC-ODS, 20×250 mm, 15 μm
3) Mobile Phase:
   Acidic condition: water containing 0.05% TFA/acetonitrile
   Basic conditions: water containing 0.01% $NH_4HCO_3$/acetonitrile In the procedures that follow, after each starting material, reference to an intermediate is typically provided. This is provided merely for assistance to the skilled chemist. The starting material may not necessarily have been prepared from the batch referred to.

Description 1 methyl 5,6-dichloronicotinate (D1)

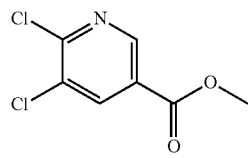

A mixture of 5,6-dichloronicotinic acid (5 g) and sulfurous dichloride (3.10 g) in methanol (20 mL) was stirred overnight at 25° C. Cold water (100 mL) was added and the resulting mixture was neutralized with sat. $NaHCO_3$ solution. The aqueous layer was extracted with DCM (2×100 mL) and the combined organic layers were dried over $Na_2SO_4$. After filtration, the filtrate was concentrated in vacuo to give the title compound (5 g) as white solid. MS (ESI): $C_7H_5Cl_2NO_2$ requires 205; found 206 $[M+H]^+$.

Description 2 methyl 5,6-dimethylnicotinate (D2)

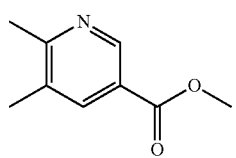

A mixture of $K_2CO_3$ (1.342 g), tricyclohexylphosphine (0.272 g), $Pd_2(dba)_3$ (0.444 g), methylboronic acid (0.291 g) and methyl 5,6-dichloronicotinate (D1, 1 g) in 1,4-dioxane (20 mL) was heated to 110° C. overnight. Cold water (30 mL) was added and the aqueous layer was extracted with DCM (2×100 mL). The combined organic layers were dried over $Na_2SO_4$, filtered and concentrated in vacuo. The resulting residue was purified by column chromatography (eluting with EA:PE=0% to 50%) to give the title compound (1 g) as yellow oil. MS (ESI): $C_9H_{11}NO_2$ requires 165; found 166 $[M+H]^+$.

Description 3

5,6-dimethylnicotinic acid (D3)

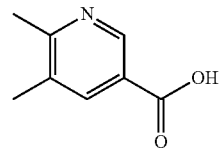

A mixture of sodium hydroxide (121 mg) and methyl 5,6-dimethylnicotinate (D2, 500 mg) in methanol (10 mL) and water (10 mL) was stirred for 2 hours. Cold water (50 mL) was added and the pH value of the resulting mixture was adjusted to 5 by HCl solution (7 M). The aqueous layer was extracted with DCM (2×100 mL). The combined organic layers were dried over $Na_2SO_4$, filtered and concentrated in vacuo to give the title compound (400 mg) as white solid. MS (ESI): $C_8H_9NO_2$ requires 151; found 152 $[M+H]^+$.

Description 4 ethyl 5-cyano-2-hydroxy-6-methylnicotinate (D4)

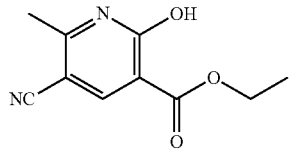

A mixture of diethyl 2-(ethoxymethylene)malonate (21.6 g) and (E)-3-aminobut-2-enenitrile (8.20 g) in a round bottom flask was stirred at 150° C. for 2 hours and standing overnight. The mixture was filtered and the precipitate was washed with ice-cold methanol to afford the title compound (5 g) as yellow solid. MS (ESI): $C_{10}H_{10}N_2O_3$ requires 206; found 207 $[M+H]^+$.

Description 5 ethyl 2-chloro-5-cyano-6-methylnicotinate (D5)

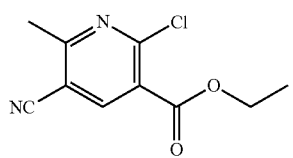

A mixture of ethyl 5-cyano-2-hydroxy-6-methylnicotinate (D4, 3000 mg) in andphosphoryl trichloride (22300 mg) in a round bottom flask was stirred at 90° C. for 5 hours and standing overnight. The solution was concentrated in vacuo. The residue was poured into ice. The resulting mixture was filtered to afford the title compound (3 g) as yellow solid. MS (ESI): $C_{10}H_9ClN_2O_2$ requires 224; found 225 $[M+H]^+$.

Description 6 ethyl 5-cyano-6-methylnicotinate (D6)

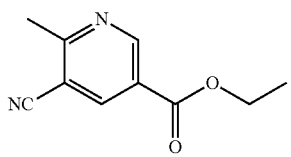

To a mixture of ethyl 2-chloro-5-cyano-6-methylnicotinate (D5, 1.5 g), methanol (50 mL) and palladium (10% on carbon, 0.071 g) was added ammonium formate (6.32 g). The mixture was stirred at RT for 3 hours, and then filtered. The solution was concentrated in vacuo. The residue was purified by column chromatography (eluting with EA:PE=20%) to afford the title compound (1 g) as white solid. MS (ESI): $C_{10}H_{10}N_2O_2$ requires 190; found 191 $[M+H]^+$.

Description 7

5-cyano-6-methylnicotinic acid (D7)

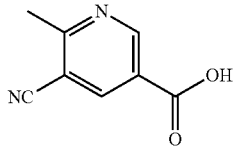

To a mixture of ethyl 5-cyano-6-methylnicotinate (D6, 1 g), methanol (15 mL) and water (30 mL) was added sodium hydroxide (2.103 g). The mixture was stirred at RT for 30 mins. The pH of the solution was adjusted to 4 with hydrochloric acid. The mixture was washed with EA (2×100 mL). The combined organic layers were concentrated in vacuo to afford the title compound (800 mg) as white solid. $^1$H NMR (400 MHz, MeOD-$d_4$): 9.20 (d, J=2.0 Hz, 1H), 8.62 (d, J=2.0 Hz, 1H), 2.83 (s, 3H). MS (BSI): $C_8H_6N_2O_2$ requires 162; found 163 $[M+H]^+$.

Description 8 methyl 2-(4-hydroxycyclohexyl)acetate (D8)

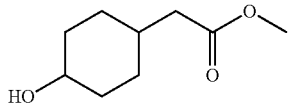

A mixture of Rh/C (1 g) and methyl 2-(4-hydroxyphenyl) acetate (2.2 g) in methanol (50 mL) was stirred at 50° C. for 6 hours under $H_2$ atmosphere (5 bar). The reaction mixture was filtered and the filtrate was concentrated in vacuo to afford the title compound (500 mg). $^1$H NMR (400 MHz, DMSO-$d_6$): 3.73 (s, 3H), 2.51 (s, 2H), 2.21-2.16 (m, 21.1), 1.72-1.32 (m, 7H), 1.19-0.91 (m, 2H).

Description 9

2-(4-hydroxycyclohexyl)acetic acid (D9)

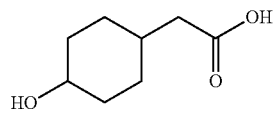 [SMILES: O=C(O)CC1CCC(O)CC1]

A mixture of potassium hydroxide (326 mg) and methyl 2-(4-hydroxycyclohexyl)acetate (D8, 500 mg) in methanol (20 mL) and water (20 mL) was stirred at 60° C. for 6 hours. After cooling to RT, the reaction mixture was concentrated and acidified with HCl solution (2 M) to adjust the pH value to 1, and then extracted with EA (50 mL). The organic layer was dried over $Na_2SO_4$, filtered and concentrated in vacuo to afford the title compound (150 mg) as white solid. MS (ESI): $C_8H_{14}O_3$ requires 158; found 159 $[M+H]^+$.

Description 10

(3,3-difluorocyclobutyl)methanol (D10)

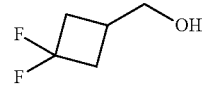

To a mixture of 3,3-difluorocyclobutanecarboxylic acid (970 mg) in THF (25 mL) cooled at 0° C. was added dropwise borane-methyl sulfide complex (1.354 mL) under $N_2$. The mixture was stirred for 4 hours at 0° C. The mixture was quenched with the conc. HCl solution. The aqueous layer was extracted with DCM (2×30 mL). The combined organic layers were dried over $Na_2SO_4$ and filtered. The residue was concentrated in vacuo to afford the title compound (650 mg) as colorless oil. $^1$H NMR (400 MHz, CDCl$_3$): 3.62 (d, J=5.2 Hz, 2H), 2.75 (brs, 1H), 2.62-2.54 (m, 2H), 2.35-2.25 (m, 3H).

Description 11

(3,3-difluorocyclobutyl)methyl 4-methylbenzenesulfonate (D11)

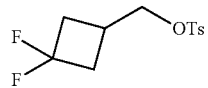

To a solution of (3,3-difluorocyclobutyl)methanol (D10, 650 mg) and TEA (1077 mg) in DCM (20 mL) was added solution of 4-methylbenzene-1-sulfonyl chloride (1218 mg)

in DCM (5 mL). The mixture was stirred overnight, and then concentrated in vacuo. The residue was purified by column chromatography (eluting with EA:PE=0% to 30%) to afford the title compound (760 mg) as white solid. $^1$H NMR (400 MHz, CDCl$_3$): 7.80 (d, J=8.4 Hz, 2H), 7.37 (d, J=8.0 Hz, 2H), 4.06 (d, J=6.4 Hz, 2H), 2.67-2.61 (m, 2H), 2.49-2.47 (m, 4H), 2.32-2.27 (m, 2H). MS (ESI): C$_{12}$H$_{14}$F$_2$O$_3$S requires 276; found 299 [M+Na]$^+$.

Description 12

2-(3,3-difluorocyclobutyl)acetonitrile (D12)

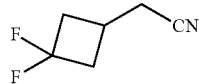

A mixture of (3,3-difluorocyclobutyl)methyl 4-methylbenzenesulfonate (D11, 720 mg) and cyanopotassium (170 mg) in DMF (6 mL) was stirred at 50° C. for 16 hours. After cooling to RT, cold water (30 mL) was added and the aqueous layer was extracted with DCM (2×30 mL). The combined organic layers were washed with brine and dried over Na$_2$SO$_4$. After filtration, the filtrate was concentrated in vacuo to afford the title compound (310 mg) as colorless oil. $^1$H NMR (400 MHz, CDCl$_3$): 2.89-2.78 (m, 2H), 2.60-2.52 (m, 3H), 2.46-2.34 (m, 2H).

Description 13

2-(3,3-difluorocyclobutyl)acetic acid (D13)

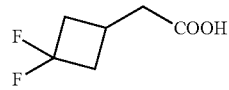

A mixture of 2-(3,3-difluorocyclobutyl)acetonitrile (D12, 300 mg) and NaOH (1830 mg) in water (5 mL) and methanol (5 mL) was stirred at 100° C. for 36 hours. After cooling to RT, aqueous HCl solution (1 M) was added to adjust the pH value to about 2. The resulting aqueous layer was extracted with DCM (2×30 mL). The combined organic layers were dried over Na$_2$SO$_4$, filtered and concentrated in vacuo to afford the title compound (120 mg) as yellow oil. $^1$H NMR (400 MHz, DMSO-d$_6$): 12.21 (brs, 1H), 2.72-2.62 (m, 2H), 2.55-2.26 (m, 5H).

Description 14 methyl 6-ethylnicotinate (D14)

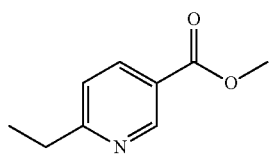

To a mixture of methyl 6-chloronicotinate (5.5 g) and ferric acetylacetonate (0.5 g) in THF (100 mL) and NMP (10 mL) was added dropwise ethylmagnesium bromide (1 M in THF, 40 mL) at 0° C. After addition the mixture was stirred at RT for 30 minutes and then poured into ice/water (300 mL). The mixture was extracted with EA (2×100 ml). The combined organic layers were dried over Na$_2$SO$_4$ and evaporated to give the crude product, which was purified by column chromatography (eluting with EA:PE=5%) to afford the title compound (2.7 g) as clear oil. MS (ESI): C$_9$H$_{11}$NO$_2$ requires 162; found 163 [M+H]$^+$.

Description 15

6-ethylnicotinic acid (D15)

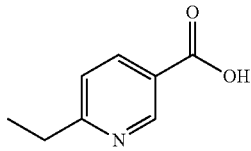

To a solution of methyl 6-ethylnicotinate (D14, 2.7 g) in THF (20 mL) was added a solution of NaOH (1.5 g) in water (20 mL). The mixture was stirred at RT for 1 hour, and then concentrated under reduced pressure. The resulting aqueous phase was acidified by HCl solution (1 M) to adjust the pH value to 3. The mixture was concentrated in vacuo and the crude product was stirred in MeOH (30 mL) at RT for 10 minutes. The suspension was filtered and the filtrate was concentrated in vacuo afford the title compound (2.5 g) as white solid. $^1$H NMR (400 MHz, MeOD-d$_4$): 9.16 (d, J=1.2 Hz, 1H), 8.88 (dd, J=8.8 Hz, 2.0 Hz, 1H), 8.01 (d, J=8.4 Hz, 1H), 3.15 (q, J=7.6 Hz, 2H), 1.45 (t, J=7.6 Hz, 3H). MS (EST): C$_9$H$_{11}$NO$_2$ requires 151; found 152 [M+H]$^+$.

Description 16 methyl 2,6-dichloro-5-fluoronicotinate (D16)

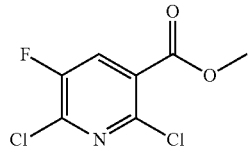

To a mixture of 2,6-dichloro-5-fluoronicotinic acid (5 g) and one drop of DMF in DCM (20 mL) was added dropwise oxalyl chloride (5 mL) at RT. The mixture was stirred at RT for 1 hour, and then concentrated. The resulting acyl chloride was again dissolved in DCM (10 mL), and then added dropwise to a mixture of DCM (20 mL) and MeOH (20 mL). The resulting mixture was stirred at RT for another 1 hour, and then concentrated to afford the title compound (6 g) as oil. MS (ESI): C$_7$H$_4$Cl$_2$FNO$_2$ requires 223; found 224 [M+H]$^+$.

Description 17 methyl 2-chloro-5-fluoro-6-methylnicotinate (D17)

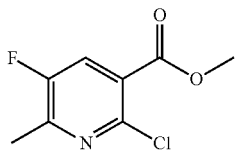

A mixture of methyl 2,6-dichloro-5-fluoronicotinate (D16, 6 g), 2,4,6-trimethyl-1,3,5,2,4,6-trioxatriborinane (3.36 g), K₂CO₃ (9.99 g) and Pd(Ph₃P)₄ (1.548 g) in 1,4-dioxane (50 mL) was heated to 110° C. for 20 hours. The mixture was filtered, and the filtrate was concentrated. The residue was purified by column chromatography (eluting with EA:PE=1:10) to afford the title compound (3.5 g) as oil. MS (ESI): $C_8H_7ClFNO_2$ requires 203; found 204 [M+H]⁺.

Description 18 methyl 5-fluoro-6-methylnicotinate (D18)

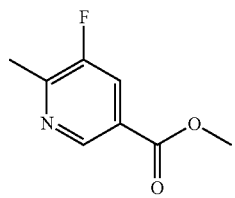

A mixture of methyl 2-chloro-5-fluoro-6-methylnicotinate (D17, 4.2 g), Pd/C (0.5 g) and sodium acetate (6.77 g) in EA (50 mL) was stirred at RT overnight under a hydrogen atmosphere (1 atm). The mixture was filtered, and the filtrate was concentrated. The residue was purified by column chromatography (EA:PE=1:10) to afford the title compound (3.5 g) as white solid. MS (ESI): $C_8H_8FNO_2$ requires 169; found 170 [M+H]⁺.

Description 19

5-fluoro 6 methylnicotinic acid (D19)

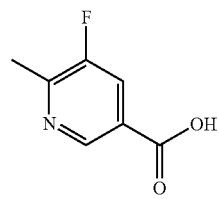

To a solution of methyl 5-fluoro-6-methylnicotinate (D18, 2.3 g) in THF (10 mL) and methanol (10 mL) was added a solution of NaOH (0.707 g) in water (5 mL). The mixture was stirred at RT for 1 hour, and then concentrated under vacuum. To the residue was added water (5 mL). The pH of the mixture was adjusted to 3. The solid was collected and dried under vacuum afford the title compound (800 mg) as white solid. ¹H NMR (400 MHz, DMSO-d₆): 8.83 (s, 1H), 8.00 (dd, J=1.2 Hz, 9.6 Hz, 1H), 2.57 (s, 3H). MS (ESI): $C_7H_6FNO_2$ requires 155; found 156 [M+H]⁺.

Description 20

5-methoxy-6-methylnicotinic acid (D20)

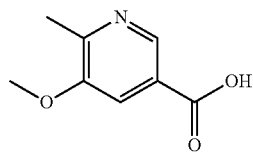

A mixture of methyl 5-fluoro-6-methylnicotinate (400 mg) and sodium methanolate (383 mg) in DMF (2 mL) was irradiated in the microwave at 120° C. for 1 hour. After cooling to RT, the mixture was acidified by aqueous HCl solution (1 M) to adjust the pH value to about 3. The aqueous layer was extracted with EA (2×30 mL). The combined organic layers were dried over anhydrous Na₂SO₄, filtered and concentrated in vacuo to afford the title compound (180 mg) as yellow solid. MS (ESI): $C_8H_9NO_3$ requires 167; found 168 [M+H]⁺.

Description 21

3-methylcyclobutanecarboxylic acid (D21)

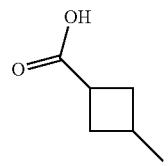

A mixture of 3-methylenecyclobutanecarboxylic acid (1 g) and Pd/C (0.19 g) in MeOH (20 mL) was stirred at RT under H₂ balloon overnight. The mixture was filtered and the filtrate was concentrated in vacuo to afford the title compound (760 mg). MS (ESI): $C_6H_{10}O_2$ requires 114. found no mass.

Description 22 tert-butyl (3-methylcyclobutyl)carbamate (D22)

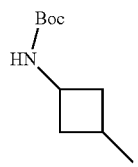

A solution of 3-methylcyclobutanecarboxylic acid (D21, 700 mg), TEA (1862 mg) and diphenylphosphinyl azide (2237 mg) in tert-butanol (10 ml) was stirred at 80° C. overnight. After cooling to RT, the mixture was filtered and the filtrate was diluted with water. The resulting mixture was further extracted with EA. The organic layer was washed with brine, dried over Na$_2$SO$_4$ and concentrated in vacuo to afford the title compound (320 mg). MS (ESI): C$_{10}$H$_{19}$NO$_2$ requires 185; found no mass.

Description 23

3-methylcyclobutanamine, hydrochloric acid salt (D23)

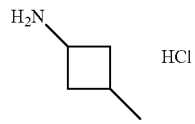

A solution of tert-butyl (3-methylcyclobutyl)carbamate (D22, 310 mg) in MeOH (5 mL) was added HCl solution (4 M in dioxane, 0.837 mL). The mixture was stirred at RT for 4 hours, and then concentrated under reduced pressure to afford the title compound (110 mg) as oil. MS (ESI): C$_5$H$_{11}$N requires 85; found no mass.

Description 24 tert-butyl (cyclopropylmethyl)carbamate (D24)

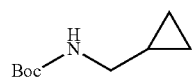

A mixture of Boc$_2$O (1.632 mL), DMAP (86 mg), TEA (711 mg) and cyclopropylmethanamine (500 mg) in DCM (20 mL) was stirred overnight at RT. Cold water (100 mL) was added and the aqueous layer was extracted with DCM (2×100 mL). The combined organic layers were dried over Na$_2$SO$_4$, filtered and concentrated in vacuo to afford the title compound (550 mg) as white solid. $^1$H NMR (400 MHz, CDCl$_3$): 3.07-3.00 (m, 2H), 1.60 (brs, 1H), 1.49 (s, 9H), 0.99-0.92 (m, 1H), 0.52-0.48 (m, 2H), 0.21-0.17 (m, 2H).

Description 25 tert-butyl (cyclopropylmethyl)(methyl)carbamate (D25)

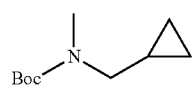

To a solution of tert-butyl (cyclopropylmethyl)carbamate (D24, 80 mg) in THF (10 mL) was added sodium hydride (56.1 mg) at 0° C. After 30 mins, iodomethane (332 mg) was added. The mixture was stirred at this temperature for 1 hour. The resulting mixture was warmed to RT and stirred overnight Cold water (30 mL) was slowly added to quench the reaction. The aqueous layer was extracted with DCM (2×50 mL). The combined organic layers were dried over Na$_2$SO$_4$, filtered and concentrated in vacuo to afford the title compound (80 mg) as yellow oil.

Description 26

1-cyclopropyl-N-methylmethanamine, hydrochloric acid salt (D26)

A mixture of tert-butyl (cyclopropylmethyl)(methyl)carbamate (D25, 80 mg) and conc. HCl (0.5 mL) in methanol (10 mL) was stirred for 3 hours. The solvent was evaporated in vacuo to afford the title compound (51 mg) as yellow solid. $^1$H NMR (400 MHz, MeOH-d$_4$): 5.51 (s, 1H), 2.92-2.90 (m, 2H), 2.72 (o, 3H), 1.10-1.07 (m, 1H), 0.76-0.70 (m, 2H), 0.45-0.4 (m, 2H).

Description 27 benzyl (cyclobutylmethyl)carbamate (D27)

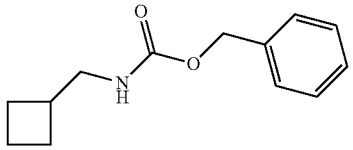 [SMILES: O=C(NCC1CCC1)OCc1ccccc1]

To a solution of cyclobutylmethanamine (150 mg) and TEA (0.246 mL) in DCM (20 mL) was added benzyl carbonochloridate (301 mg). The mixture was stirred at RT for 2 hours. The mixture was concentrated in vacuo and the residue was purified by column chromatography (eluting with EA:PE=1:15) to afford the title compound (300 mg) as colorless oil. MS (ESI): C$_{13}$H$_{17}$NO$_2$ requires 219; found 220 [M+H]$^+$.

Description 28 benzyl (cyclobutylmethyl)(methyl)carbamate (D28)

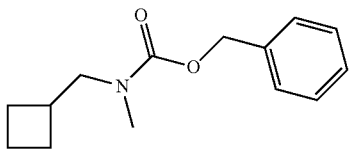 [SMILES: CN(CC1CCC1)C(=O)OCc1ccccc1]

To a solution of benzyl (cyclobutylmethyl)carbamate (D27, 300 mg) in THF (20 mL) was added NaH (60%, 328 mg) and the mixture was stirred at RT for 30 minutes. Then iodomethane (0.257 mL) was added to the above mixture and the reaction was stirred at RT for 2 hours. The mixture was quenched with water (0.1 mL) and concentrated in vacuo to give the crude product which was purified by column chromatography (eluting with EA:PE=1:5) to afford the title compound (220 mg) as colorless oil. MS (ESI): C$_{14}$H$_{19}$NO$_2$ requires 233; found 234 [M+H]$^+$.

Description 29

1-cyclobutyl-N-methylmethanamine (D29)

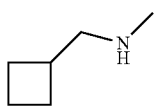

A mixture of benzyl (cyclobutylmethyl)(methyl)carbamate (D28, 220 mg) and Pd/C (20 mg) in MeOH (20 mL) was bubbled with $H_2$ at RT for 2 hours. The mixture was filtered through a celite pad and the filtrate was concentrated in vacuo to afford the title compound (90 mg) as colorless oil.

Description 30

5-fluoro-2-methyl-3-nitrobenzoic acid (D30)

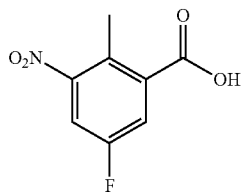

5-Fluoro-2-methylbenzoic acid (20 g) was added portionwise to ice-cooled conc. sulfuric acid (98%, 80 mL). The mixture was stirred at 0° C. until all solid dissolved. A mixture of nitric acid (65%, 6 mL) and $H_2SO_4$ (98%, 12 mL) was added portionwise. The mixture was allowed to warm gradually to RT, and stirred at RT for 6 hours. The resulting mixture was poured into ice (500 mL). The solid was collected and washed with water (100 mL). The solid was redissolved in EA (200 mL) and washed with brine. The organic layer was dried over anhydrous $Na_2SO_4$ and concentrated in vacuo to afford the title compound (11 g) as brown solid. MS (ESI): $C_8H_6FNO_4$ requires 199; found 198 [M-H]⁻.

Description 31

(5-fluoro-2-methyl-3-nitrophenyl)methanol (D31)

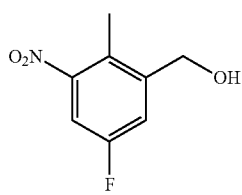

A mixture of 5-fluoro-2-methyl-3-nitrobenzoic acid (D30, 11 g) and $BH_3 \cdot THF$ (1 M, 72 mL) was heated to 80° C. for 2 hours. MeOH (20 mL) was added slowly to the mixture to quench the reaction. The resulting mixture was concentrated in vacuo. The residue was dissolved in DCM (50 mL) and washed with sat. $NaHCO_3$ solution (2×50 mL) and brine (2×50 mL). The organic phase was dried over $Na_2SO_4$, filtered and concentrated to afford the title compound (9 g) as yellow solid. MS (ESI): $C_8H_8FNO_3$ requires 185; found no mass.

Description 32

5-fluoro-2-methyl-3-nitrobenzaldehyde (D32)

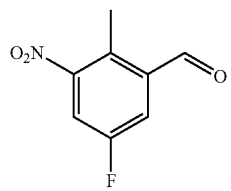

To a mixture of (5-fluoro-2-methyl-3-nitrophenyl)methanol (D31, 9 g) in DCM (100 mL) was added PCC (14 g) portionwise. The mixture was stirred at RT overnight. The solvent was removed in vacuo to give the crude product, which was purified by column chromatography (eluting with EA:PE=1:20) to afford the title compound (5 g) as pale yellow solid. MS (ESI): $C_8H_6FNO_3$ requires 185; found no mass.

Description 33

5-bromo-2-methyl-3-nitrobenzoic acid (D33)

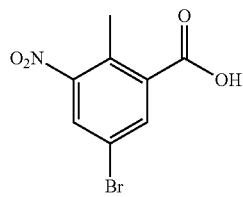

2-Methyl-3-nitrobenzoic acid (5 g) was dissolved in conc. $H_2SO_4$ (20 mL) at 0° C. To this solution, NBS (6.2 g) was added gradually. The resulting mixture was stirred at 0° C. for 2 hours, and then warmed to 40° C. After stirring at 40° C. for 3 hours, the mixture was poured into ice/water. The white solid precipitate was filtered and dried to afford the title compound (7 g) as off-white solid. MS (ESI): $C_8H_6BrNO_4$ requires 259; found no mass.

Description 34

5-chloro-2-methyl-3-nitrobenzoic acid (D34)

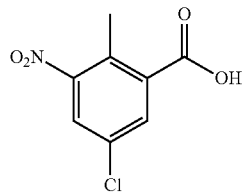

To a solution of 5-chloro-2-methylbenzoic acid (50 g) in conc. $H_2SO_4$ (300 mL) at 0° C. was added a mixture of nitric acid (65%, 1.92 g) and conc. sulfuric acid (50 mL) portionwise. The mixture was stirred for 6 hours, and then poured into ice (1 kg). The resulting mixture was diluted with water (100 mL). After filtration, the solid was collected and redissolved in EA (300 mL). The solution was washed with brine, dried over $Na_2SO_4$, filtered and concentrated in vacuo. The residue was washed with EA and PE (2:1, 50 mL) twice to afford the title compound (39 g) as yellow solid. MS (ESI): $C_8H_6ClNO_4$ requires 215; found 216 $[M+H]^+$.

Description 35

(S)-tert-butyl 4-(5-chloro-2-methyl-3-nitrobenzoyl)-2-methylpiperazine-1-carboxylate (D35)

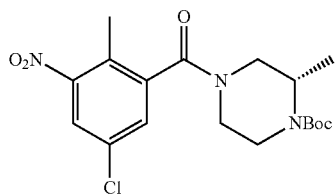 [SMILES: Cc1c(C(=O)N2CCN(C(=O)OC(C)(C)C)[C@@H](C)C2)cc(Cl)cc1[N+](=O)[O-]]

To a solution of 5-chloro-2-methyl-3-nitrobenzoic acid (D34, 32.3 g), (S)-tert-butyl 2-methylpiperazine-1-carboxylate (25 g) and DIPEA (43.6 mL) in DMF (100 mL) was added HATU (57.0 g) at 0° C. The mixture was stirred at RT overnight, and then poured into water. The resulting mixture was filtered. The solid was dissolved in EA, and washed with brine for three times. The organic solution was dried with $Na_2SO_4$ and concentrated in vacuo to afford the title compound (47 g) as light orange solid. MS (ESI): $C_{18}H_{24}ClN_3O_5$ requires 397; found 342 $[M-tBu+H+H]^+$.

Description 36

(S)-tert-butyl 4-(5-bromo-2-methyl-3-nitrobenzoyl)-2-methylpiperazine-1-carboxylate (D36)

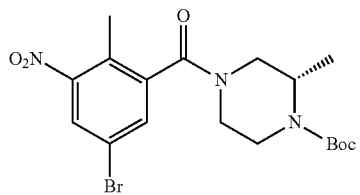 [SMILES: Cc1c(C(=O)N2CCN(C(=O)OC(C)(C)C)[C@@H](C)C2)cc(Br)cc1[N+](=O)[O-]]

D36 was prepared using a similar procedure to that described for D35. MS (ESI): $C_{18}H_{24}BrN_3O_5$ requires 441; found 464 $[M+Na]^+$.

Description 37

(S)-tert butyl 4-(5-bromo-2-methyl-3-nitrobenzyl)-2-methylpiperazine-1-carboxylate (D37)

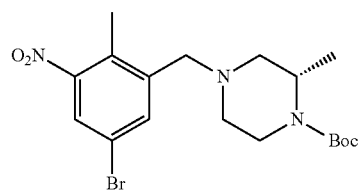 [SMILES: Cc1c(CN2CCN(C(=O)OC(C)(C)C)[C@@H](C)C2)cc(Br)cc1[N+](=O)[O-]]

(S)-tert-butyl 4-(5-bromo-2-methyl-3-nitrobenzoyl)-2-methylpiperazine-1-carboxylate (D36, 3.8 g) was dissolved in THF (20 mL) at 0° C. To this solution, $NaBH_4$ (1.625 g) was added gradually under an ice bath. Then $BF_3.OEt_2$ (5.44 mL) was added dropwise carefully. The mixture was stirred at 0° C. for 2 hours and at RT overnight. Methanol was added to quench the reaction. After removal of the solvent, the residue was extracted with EA (2×20 mL) and water (2×20 mL). The combined organic phases were dried over sodium sulfate and concentrated in vacuo to afford the title compound (4.28 g) as pale yellow oil. MS (ESI): $C_{18}H_{26}BrN_3O_4$ requires 427; found 428 $[M+H]^+$.

Description 38

(S)-tert-butyl 4-(5-fluoro-2-methyl-3-nitrobenzyl)-2-methylpiperazine-1-carboxylate (D38)

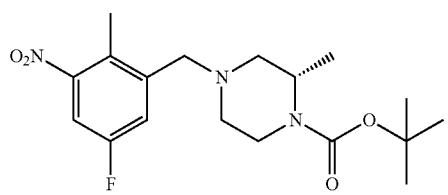 [SMILES: Cc1c(CN2CCN(C(=O)OC(C)(C)C)[C@@H](C)C2)cc(F)cc1[N+](=O)[O-]]

To a solution of 5-fluoro-2-methyl-3-nitrobenzaldehyde (D32, 10 g) and (S)-tert-butyl 2-methylpiperazine-1-carboxylate (12.03 g) in DCM (120 mL) was added drops of acetic acid (3.28 g). The mixture was stirred at RT for an hour. Sodium triacetoxyhydroborate (23.15 g) was added in ice-bath. The mixture was stirred at RT overnight and quenched with sat. $NaHCO_3$ solution. The organic layer was dried with anhydrous $Na_2SO_4$, filtered and concentrated in vacuo to afford the title compound (22.17 g). MS (ESI): $C_{18}H_{26}FN_3O_4$ requires 367; found 368 $[M+H]^+$.

Description 39

(S)-tert-butyl 4-(5-chloro-2-methyl-3-nitrobenzyl)-2-methylpiperazine-1-carboxylate (D39)

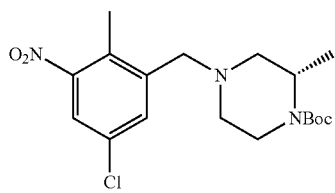

BH$_3$.THF (1.0 M in THF, 151 mL) was added dropwise to a solution of (S)-tert-butyl 4-(5-chloro-2-methyl-3-nitrobenzoyl)-2-methylpiperazine-1-carboxylate (D35, 30 g) in THF (200 mL) at 0° C. in 10 mins. The reaction mixture was heated to 75° C. and stirred for 1 hour, and concentrated in vacuo to afford the title compound (28 g) as yellow oil. MS (ESI): C$_{18}$H$_{26}$ClN$_3$O$_4$ requires 383; found 384 [M+H]$^+$.

Description 40

(S)-tert-butyl 4-(5-cyano-2-methyl-3-nitrobenzyl)-2-methylpiperazine-1-carboxylate (D40)

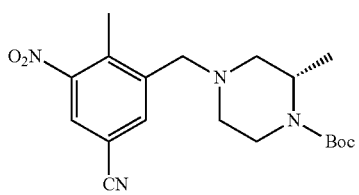

A mixture of (S)-tert-butyl 4-(5-bromo-2-methyl-3-nitrobenzyl)-2-methylpiperazine-1-carboxylate (D37, 1.28 g), dicyanozine (0.505 g) and tetrakis(triphenylphosphine)palladium(0) (0.276 g) in a sealed tube was stirred at 150° C. in the microwave for 5 hours. The reaction mixture was diluted with EA (20 mL), poured into water (50 mL), and then filtrated. The filtrate was extracted with EA (20 mL). The organic phase was washed, dried and concentrated. The residue was purified by column chromatography (eluting with EA:PE=10% to 30%) to afford the title compound (370 mg). MS (ESI): C$_{19}$H$_{26}$N$_4$O$_4$ requires 374; found 397 [M+Na]$^+$.

Description 41

(S)-tert-butyl 4-(3-amino-5-chloro-2-methylbenzyl)-2-methylpiperazine-1-carboxylate (D41)

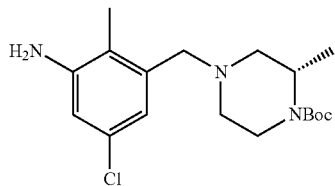 [SMILES: Cc1c(CN2CCN(C(=O)OC(C)(C)C)[C@@H](C)C2)cc(Cl)cc1[N+](=O)[O-]]

To a solution of (S)-tert-butyl 4-(5-chloro-2-methyl-3-nitrobenzyl)-2-methylpiperazine-1-carboxylate (D39, 30 g) and nickel (4.59 g) in methanol (200 mL) stirred under a nitrogen atmosphere at 50° C. was added hydrazine (80%, 12.26 mL). The reaction mixture was stirred at 50° C. for 1 hour. The catalyst was filtered, and the filtrate was concentrated. The residue was dried in vacuo to afford the title compound (27 g) as light yellow oil. MS (ESI): C$_{18}$H$_{28}$ClN$_3$O$_2$ requires 353; found 354 [M+H]$^+$.

Description 42

(S)-tert-butyl 4-(3-amino-5-cyano-2-methylbenzyl)-2-methylpiperazine-1-carboxylate (D42)

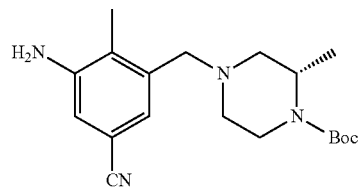

To a solution of (S)-tert-butyl 4-(5-cyano-2-methyl-3-nitrobenzyl)-2-methylpiperazine-1-carboxylate (D40, 1010 mg) in ethanol (10 mL) was added tin(II) chloride dihydrate (2587 mg). The mixture was stirred at RT overnight. The pH value of the mixture was adjusted to about 8 by sodium bicarbonate solution. The white precipitate was filtered by celite. The filtrate was concentrated, and then extracted with EA (2×20 mL). The combined organic phases were washed with water (2×10 mL). The resulting organic phases were concentrated in vacuo to afford the title compound (630 mg) as yellow oil. MS (ESI): C$_{19}$H$_{28}$N$_4$O$_2$ requires 344; found 345 [M+H]$^+$.

Description 43

(S)-1-(5-fluoro-2-methyl-3-nitrobenzyl)-3-methylpiperazine, 2 hydrochloric acid salt (D43)

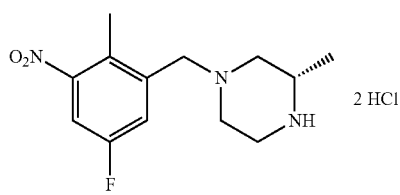 [SMILES: Cc1c(CN2CCN[C@@H](C)C2)cc(F)cc1[N+](=O)[O-]]

To a solution of (S)-tert-butyl 4-(5-fluoro-2-methyl-3-nitrobenzyl)-2-methylpiperazine-1-carboxylate (D38, 4 g) in DCM (15 mL) was added hydrogen chloride/MeOH (27.2 mL). The mixture was degassed and stirred under a nitrogen atmosphere at RT for 12 hours. The mixture was concentrated in vacuo afford the title compound (3.1 g). MS (ESI): C$_{13}$H$_{18}$FN$_3$O$_2$ requires 267; found 268 [M+H]$^+$.

Description 44

(S)-1-(5-chloro-2-methyl-3-nitrobenzyl)-3-methyl-piperazine (D44)

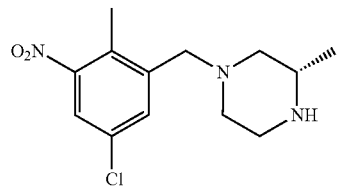 [SMILES: Cc1c(CN2CCN[C@@H](C)C2)cc(Cl)cc1[N+](=O)[O-]]

To a solution of (S)-tert-butyl 4-(5-chloro-2-methyl-3-nitrobenzyl)-2-methylpiperazine-1-carboxylate (D39, 1.5138 g) in DCM (15 mL) was added TFA (3.04 mL) dropwise. The resulting mixture was stirred overnight at RT. The solvent was removed under vacuum. The residue was diluted with DCM (10 mL), and neutralized with sat. $Na_2CO_3$ solution to pH=9. Then NaOH solution (2 M) was added to adjust pH value to 11. The aqueous phase was separated, and extracted with DCM (2×15 mL). The combined organic layers were dried over $Na_2SO_4$, filtered and concentrated in vacuo to afford the title compound (1.17 g) as pale yellow oil. MS (ESI): $C_3H_{18}ClN_3O_2$ requires 283; found 284 $[M+H]^+$.

Description 45

(S)-cyclopentyl 4-(5-chloro-2-methyl-3-nitrobenzyl)-2-methylpiperazine-1-carboxylate (D45)

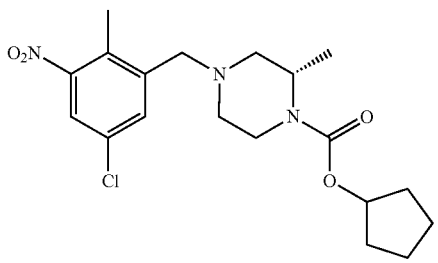 [SMILES: Cc1c(CN2CCN(C(=O)OC3CCCC3)[C@@H](C)C2)cc(Cl)cc1[N+](=O)[O-]]

To a solution of (S)-1-(5-chloro-2-methyl-3-nitrobenzyl)-3-methylpiperazine (D44, 489 mg) and TEA (0.426 mL) in THF (5 mL) was added cyclopentyl carbonochloridate (340 mg). The mixture Was stirred at RT overnight. The mixture was dissolved in EA (20 mL) and then washed with water (3×10 mL). The organic layer was dried over anhydrous $Na_2SO_4$, filtered and concentrated in vacuo to afford the title compound (530 mg) as yellow oil. MS (ESI): $C_{19}H_{26}ClN_3O_4$ requires 395; found 396 $[M+H]^+$.

Description 46

(S)-4-(5-chloro-2-methyl-3-nitrobenzyl)-N-(cyclopropylmethyl)-2-methylpiperazine-1-carboxamide (D46)

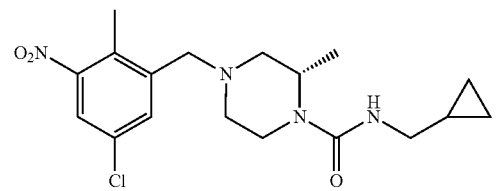 [SMILES: Cc1c(CN2CCN(C(=O)NCC3CC3)[C@@H](C)C2)cc(Cl)cc1[N+](=O)[O-]]

The mixture of (S)-1-(5-chloro-2-methyl-3-nitrobenzyl)-3-methylpiperazine (D44, 800 mg), TEA (1.965 mL) and triphosgene (669 mg) in THF (20 mL) was stirred at 0° C. for 30 minutes. Then cyclopropylmethanamine (201 mg) was added and the mixture was stirred at RT for 20 hours. The mixture was concentrated in vacuo and the crude product was purified by column chromatography (eluting with EA:PE=1:10 to 1:2) to afford the title compound (780 mg) as colorless oil. MS (ESI): $C_{18}H_{25}ClN_4O_3$ requires 380; found 381 $[M+H]^+$.

Description 47-51

Descriptions 47-51 were prepared using a similar procedure to that described for D46, with the specified reaction solvent and base listed in the table.

D47: (S)-cyclopropylmethyl 4-(5-chloro-2-methyl-3-nitrobenzyl)-2-methylpiperazine-1-carboxylate
D48: (S)-(4-(5-chloro-2-methyl-3-nitrobenzyl)-2-methylpiperazin-1-yl)(pyrrolidin-1-yl)methanone
D49: (S)-(4-(5-chloro-2-methyl-3-nitrobenzyl)-2-methylpiperazin-1-yl)(piperidin-1-yl)methanone
D50: (S)-(4-(5-chloro-2-methyl-3-nitrobenzyl)-2-methylpiperazin-1-yl)(3-methylazetidin-1-yl)methanone
D51: (S)-(4-(5-fluoro-2-methyl-3-nitrobenzyl)-2-methylpiperazin-1-yl)(pyrrolidin-1-yl)methanone

| | Structure | solvent/base | Characterization |
|---|---|---|---|
| D47 | 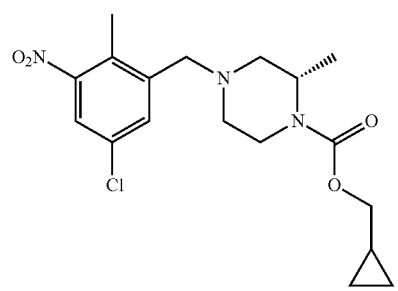 | DCM/DIPEA | MS (ESI): $C_{18}H_{24}ClN_3O_4$ requires 381; found 382 $[M + H]^+$. |

-continued

| | Structure | solvent/base | Characterization |
|---|---|---|---|
| D48 | 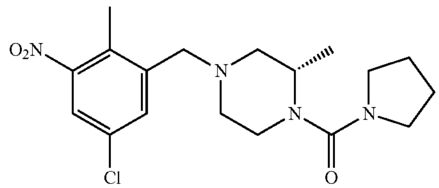 | THF/DIPEA | MS (ESI): $C_{18}H_{25}ClN_4O_3$ requires 380; found 381 $[M + H]^+$. |
| D49 | 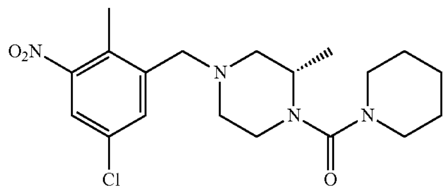 | THF/DIPEA | MS (ESI): $C_{19}H_{27}ClN_4O_3$ requires 394; ound 395 $[M + H]^+$. |
| D50 | 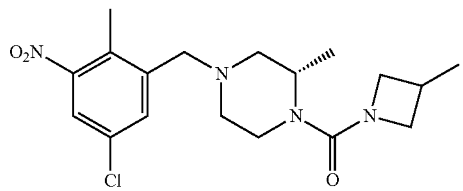 | DCM/DIPEA | MS (ESI): $C_{18}H_{25}ClN_4O_3$ requires 380; found 381 $[M + H]^+$. |
| D51 | 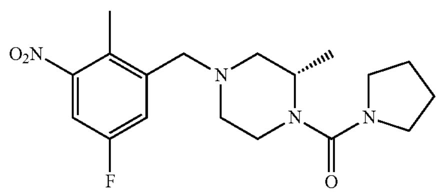 | DCM/DIPEA | MS (ESI): $C_{18}H_{25}FN_4O_3$ requires 364; found 365 $[M + H]^+$. |

Description 52

(S)-cyclopentyl 4-(3-amino-5-chloro-2-methylbenzyl)-2-methylpiperazine-1-carboxylate (D52)

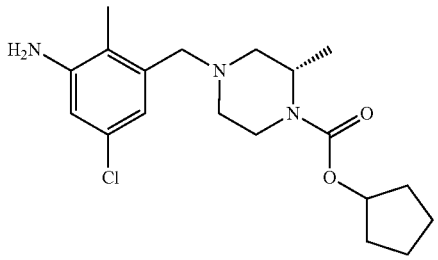

To a solution of compound (S)-cyclopentyl 4-(5-chloro-2-methyl-3-nitrobenzyl)-2-methylpiperazine-1-carboxylate (D45, 530 mg) in ethanol (10 mL) was added final) chloride dihydrate (1284 mg). The mixture was stirred at RT overnight. The pH value of the mixture was adjusted to about 8 by aqueous sodium bicarbonate solution. The white precipitate was filtered by celite and the filtrate was concentrated in vacuo. The resulting residue was extracted with EA (2×20 mL). The combined organic layers were washed with water (2×10 mL) and dried over anhydrous $Na_2SO_4$. After filtration, the filtrate was concentrated in vacuo to afford the title compound (418 mg) as yellow oil. MS (ESI). $C_{19}N_{28}ClN_3O_2$ requires 365; found 366 $[M+H]^+$.

Description 53

(S)-cyclopropylmethyl 4-(3-amino-5-chloro-2-methylbenzyl)-2-methylpiperazine-1-carboxylate (D53)

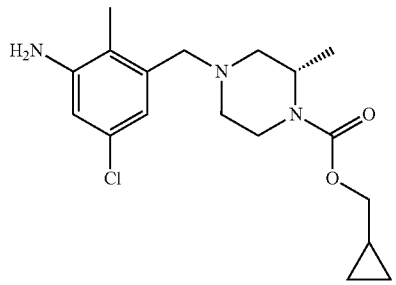 [SMILES: Cc1c(CN2CCN(C(=O)OCC3CC3)[C@@H](C)C2)cc(Cl)cc1[N+](=O)[O-]]

D53 was prepared using a similar procedure to that described for D52. MS (ESI): $C_{18}H_{26}ClN_3O_2$ requires 351; found 352 $[M+H]^+$.

Description 54

(S)-4-(3-amino-5-chloro-2-methylbenzyl)-N-(cyclopropylmethyl)-2-methylpiperazine-1-carboxamide (D54)

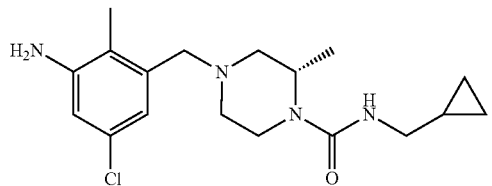

To a solution of (S)-4-(5-chloro-2-methyl-3-nitrobenzyl)-N-(cyclopropylmethyl)-2-methylpiperazine-1-carboxamide (D46, 780 mg) in methanol (50 mL) was added sat. ammonium chloride (1095 mg) solution and iron (915 mg). The mixture was then stirred at RT for 1 hour. The mixture was filtered through a celite pad and washed with MeOH. The filtrate was concentrated and partitioned between EA and water. The organic layer was dried over $Na_2SO_4$, filtered and concentrated in vacuo to afford the title compound (670 mg) as colorless oil. MS (ESI): $C_{18}H_{27}ClN_4O$ requires 350; found 351 [M+H]$^+$.

Description 55-58

Descriptions 55 to 58 were prepared using a similar procedure to that described for Description 54.

D55: (S)-(4-(3-amino-5-chloro-2-methylbenzyl)-2-methylpiperazin-1-yl)(pyrrolidin-1-yl)methanone
D56: (S)-(4-(3-amino-5-chloro-2-methylbenzyl)-2-methylpiperazin-1-yl)(piperidin-1-yl)methanone
D57: (S)-(4-(3-amino-5-chloro-2-methylbenzyl)-2-methylpiperazin-1-yl)(3-methylazetidin-1-yl)methanone
D58: (S)-(4-(3-amino-5-fluoro-2-methylbenzyl)-2-methylpiperazin-1-yl)(pyrrolidin-1-yl)methanone

| | Structure | Characterization |
|---|---|---|
| D55 | 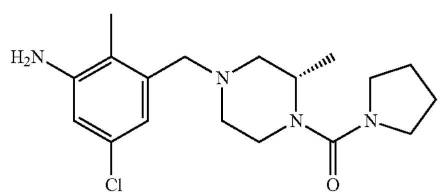 | MS (ESI): $C_{18}H_{27}ClN_4O$ requires 350; found 351 [M + H]$^+$. |
| D56 | 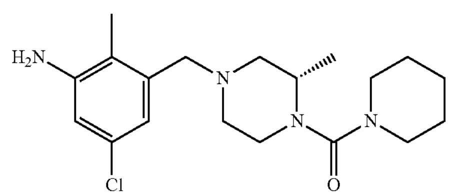 | MS (ESI): $C_{19}H_{29}ClN_4O$ requires 364; found 365 [M + H]$^+$. |
| D57 | 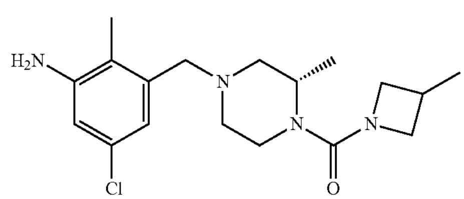 | MS (ESI): $C_{18}H_{27}ClN_4O$ requires 350; found 351 [M + H]$^+$. |
| D58 | 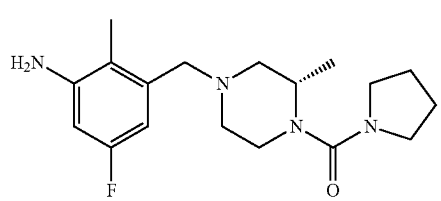 | MS (ESI): $C_{18}H_{27}FN_4O$ requires 334; found 335 [M + H]$^+$. |

Description 59 tert-butyl 3-(2-((5-chloro-3-(((S)-4-((cyclopropylmethyl)carbamoyl)-3-methylpiperazin-1-yl)methyl)-2-methylphenyl)amino)-2-oxoethyl)pyrrolidine-1-carboxylate (D59)

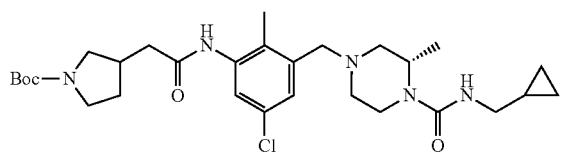 [SMILES: Cc1c(CN2CCN(C(=O)NCC3CC3)[C@@H](C)C2)cc(Cl)cc1NC(=O)CC1CCN(C(=O)OC(C)(C)C)C1]

A mixture of EDC (82 mg), HOBT (43.6 mg), 2-(1-(tert-butoxycarbonyl)pyrrolidin-3-yl)acetic acid (65.3 mg) and (S)-4-(3-amino-5-chloro-2-methylbenzyl)-N-(cyclopropylmethyl)-2-methylpiperazine-1-carboxamide (D54, 100 mg) in DCM (10 mL) was stirred at 25° C. for 2 days. Cold water (50 mL) was added and the aqueous layer was extracted with DCM (2×100 mL). The combined organic layers were dried over Na$_2$SO$_4$, filtered and concentrated in vacuo. The resulting residue was purified by column chromatography (eluting with EA:PE=0% to 100%) to afford the title compound (150 mg). MS (ESI): C$_{29}$H$_{44}$ClN$_5$O$_4$ requires 561; found 562 [M+H]$^+$.

Description 60 tert-butyl 2-(2-((5-chloro-3-(((S)-4-((cyclopropylmethyl)carbamoyl)-3-methylpiperazin-1-yl)methyl)-2-methylphenyl)amino)-2-oxoethyl)pyrrolidine-1-carboxylate (D60)

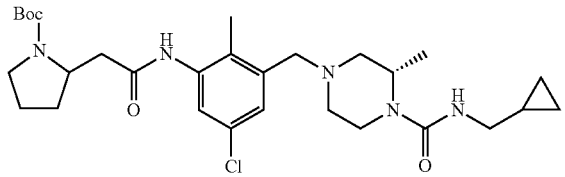 [SMILES: Cc1c(CN2CCN(C(=O)NCC3CC3)[C@@H](C)C2)cc(Cl)cc1NC(=O)CC1CCCN1C(=O)OC(C)(C)C]

D60 was prepared using a similar procedure to that described for D59, with DCM/DIPEA as the solvent/base. MS (ESI): C$_{29}$H$_{44}$ClN$_5$O$_4$ requires 561; found 562 [M+H]$^+$.

Description 61

(2S)-4-(5-chloro-2-methyl-3-(2-(pyrrolidin-3-yl)acetamido)benzyl)-N-(cyclopropylmethyl)-2-methylpiperazine-1-carboxamide, 2 hydrochloric acid salt (D61)

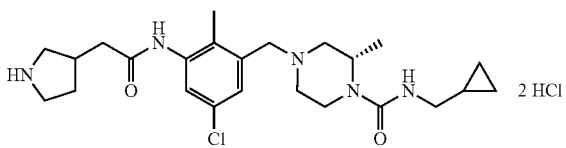 [SMILES: Cc1c(CN2CCN(C(=O)NCC3CC3)[C@@H](C)C2)cc(Cl)cc1NC(=O)CC1CCNC1]

A mixture of tert-butyl 3-(2-((5-chloro-3-(((S)-4-((cyclopropylmethyl)carbamoyl)-3-methylpiperazin-1-yl)methyl)-2-methylphenyl)amino)-2-oxoethyl)pyrrolidine-1-carboxylate (D59, 120 mg) and HCl solution (4 M in dioxane, 1 mL) was stirred for 2 hours. The solvent was evaporated to afford the title compound (100 mg) as yellow solid. MS (ESI): C$_{24}$H$_{36}$ClN$_5$O$_2$ requires 461; found 462 [M+H]$^+$.

Description 62

(2S)-4-(5-chloro-2-methyl-3-(2-(pyrrolidin-2-yl)acetamido)benzyl)-N-(cyclopropylmethyl)-2-methylpiperazine-1-carboxamide, 2 hydrochloric acid salt (D62)

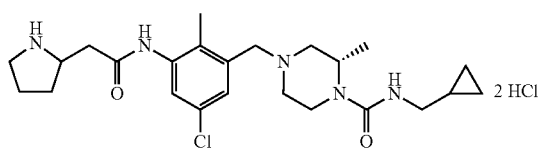 [SMILES: Cc1c(CN2CCN(C(=O)NCC3CC3)[C@@H](C)C2)cc(Cl)cc1NC(=O)CC1CCCN1]

To a solution of tert-butyl 2-(2-((5-chloro-3-(((S)-4-((cyclopropylmethyl)carbamoyl)-3-methylpiperazin-1-yl)methyl)-2-methylphenyl)amino)-2-oxoethyl)pyrrolidine-1-carboxylate (D60, 50 mg) in methanol (10 mL) was added conc. HCl (180 mg). The mixture was stirred at 60° C. for 3 hours. After cooling to RT, the mixture was concentrated in vacuo to afford the title compound (30 mg) as white solid. MS (ESI): C$_{24}$H$_{36}$ClN$_5$O$_2$ requires 461; found 462 [M+H]$^+$.

Description 63

(S)-tert-butyl 4-(5-chloro-3-(5-fluoro-6-methylnicotinamido)-2-methylbenzyl)-2-methylpiperazine-1-carboxylate (D63)

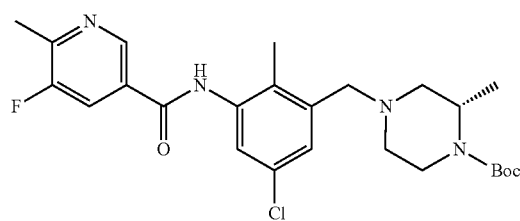 [SMILES: Cc1ncc(C(=O)Nc2cc(Cl)cc(CN3CCN(C(=O)OC(C)(C)C)[C@@H](C)C3)c2C)cc1F]

A solution of (S)-tert-butyl 4-(3-amino-5-chloro-2-methylbenzyl)-2-methylpiperazine-1-carboxylate (D41, 913 mg), 5-fluoro-6-methylnicotinic acid (D19, 400 mg), HATU (980 mg) and DIPEA (0.450 mL) in DCM (100 mL) was stirred at RT for 18 hours. The mixture was concentrated in vacuo to afford the title compound (1.2 g) as red oil. MS (ESI): C$_{25}$H$_{32}$ClFN$_4$O$_3$ requires 490; found 491 [M+H]$^+$.

Description 64

(S)-tert-butyl 4-(5-chloro-2-methyl-3-(6-methylnicotinamido)benzyl)-2-methylpiperazine-1-carboxylate (D64)

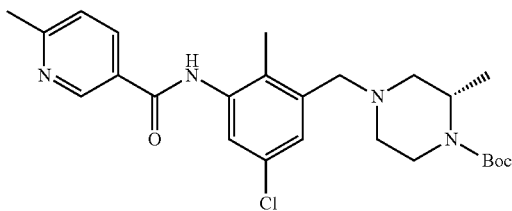 [SMILES: Cc1ccc(C(=O)Nc2cc(Cl)cc(CN3CCN(C(=O)OC(C)(C)C)[C@@H](C)C3)c2C)cn1]

To a mixture of 6-methylnicotinic acid, hydrochloric acid salt (450 mg) in DCM (10 mL) was slowly added oxalyl chloride (1 mL). The mixture was stirred for 0.5 hour at RT. The mixture was concentrated in vacuo and the residue was diluted with DCM (10 mL) and the solution was slowly added to a solution of (S)-tert-butyl 4-(3-amino-5-chloro-2-methylbenzyl)-2-methylpiperazine-1-carboxylate (D41, 1.1 g) and DIPEA (1.07 mL) in DCM (10 mL). The mixture was stirred for 1 hour at RT. Cold water (30 mL) was added and the mixture was extracted with DCM (2×100 mL). The combined organic layers were dried over $Na_2SO_4$, filtered and concentrated in vacuo. The resulting residue was purified by column chromatography (eluting with EA:PE=1:1) to afford the title compound (1 g) as purple oil. MS (ESI): $C_{25}H_{33}ClN_4O_3$ requires 472; found 473 $[M+H]^+$.

Description 65-66

Descriptions 65-66 were prepared using a similar procedure to that described for Description 64, with the specified reaction solvent and base listed in the table.

D65: (S)-tert-butyl 4-(5-chloro-3-(5-methoxy-6-methylnicotinamido)-2-methylbenzyl)-2-methylpiperazine-1-carboxylate D66: (S)-tert-butyl 4-(5-cyano-2-methyl-3-(6-methylnicotinamido)benzyl)-2-methylpiperazine-1-carboxylate

Description 67

(S)-N-(5-chloro-2-methyl-3-((3-methylpiperazin-1-yl)methyl)phenyl)-5-fluoro-6-methylnicotinamide, 2 trifluoroacetic acid salt (D67)

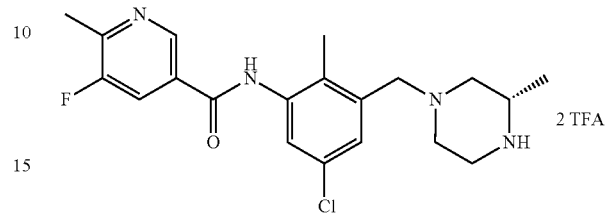

To a solution of (S)-tert-butyl 4-(5-chloro-3-(5-fluoro-6-methylnicotinamido)-2-methylbenzyl)-2-methylpiperazine-1-carboxylate (D63, 1.2 g) in DCM (20 mL) was added TFA (1.883 mL). The mixture was stirred at RT for 2 hours. The mixture was concentrated in vacuo to afford the title compound (900 mg) as yellow solid. MS (ESI): $C_{21}H_{27}ClN_4O_2$ requires 390; found 391 $[M+H]^+$.

Description 68

(S)-N-(5-chloro-2-methyl-3-((3-methylpiperazin-1-yl)methyl)phenyl)-5-methoxy-6-methylnicotinamide, 2 hydrochloric acid salt (D68)

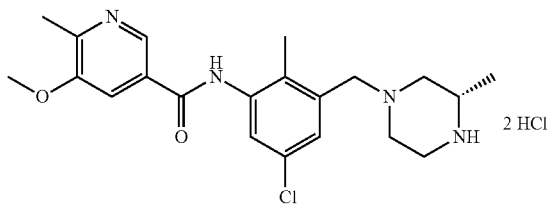

| | Structure | Solvent/base | Characterization |
|---|---|---|---|
| D65 | 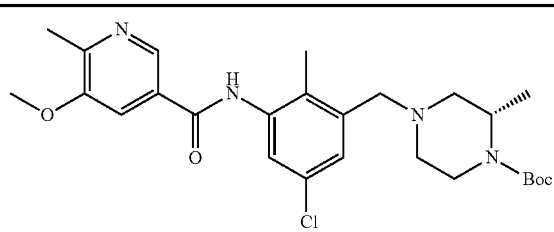 | DCM/DIPEA | MS (ESI): $C_{26}H_{35}ClN_4O_4$ requires 502; found 503 $[M + H]^+$. |
| D66 | 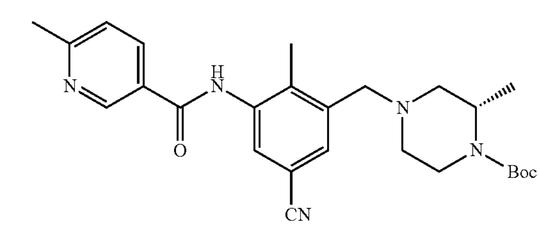 [SMILES: Cc1ccc(C(=O)Nc2cc(C#N)cc(CN3CCN(C(=O)OC(C)(C)C)[C@@H](C)C3)c2C)cn1] | DCM/Acetonitrile/$K_2CO_3$ | MS (ESI): $C_{26}H_{33}N_5O_3$ requires 463; found 464 $[M + H]^+$. |

To a solution of (S)-tert-butyl 4-(5-chloro-3-(5-methoxy-6-methylnicotinamido)-2-methylbenzyl)-2-methylpiperazine-1-carboxylate (D65, 80 mg) in MeOH (20 mL) was added HCl solution (4 M in dioxane, 0.112 mL). After stirring at 60° C. for 4 hours, the mixture was concentrated in vacuo to afford the title compound (100 mg) as white solid. MS (ESI): $C_{21}H_{27}ClN4O_2$ requires 402; found 403 $[M+H]^+$.

Description 69

(S)-N-(5-chloro-2-methyl-3-((3-methylpiperazin-1-yl)methyl)phenyl)-6-methylnicotinamide, 2 hydrochloric acid salt (D69)

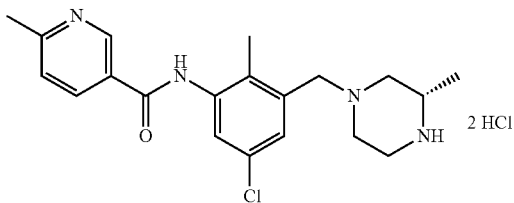

A mixture of (S)-tert-butyl 4-(5-chloro-2-methyl-3-(6-methylnicotinamido)benzyl)-2-methylpiperazine-1-carboxylate (D64, 1.0 g) in DCM (6 mL) was added HCl solution (4 M in dioxane, 1.057 mL). The mixture was stirred at RT for 2 hours, and then concentrated in vacuo to afford the title compound (1.07 g) as light yellow solid. MS (ESI): $C_{20}H_{25}ClN_4O$ requires 372. found 373 $[M+H]^+$.

Description 70

(S)-N-(5-cyano-2-methyl-3-((3-methylpiperazin-1-yl)methyl)phenyl)-6-methylnicotinamide, 2 hydrochloric acid salt (D70)

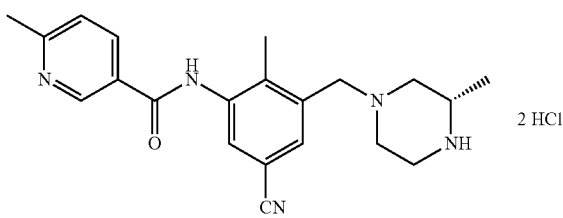

(S)-tert-butyl 4-(5-cyano-2-methyl-3-(6-methylnicotinamido)benzyl)-2-methylpiperazine-1-carboxylate (D66, 300 mg) was added into HCl solution (5 M in isopropanol, 1.294 mL) in ethanol (20 mL). The reaction mixture was stirred at 80° C. overnight. The solvent was removed in vacuo and the residue was triturated in EA to afford the title compound (280 mg) as white solid. MS (ESI): $C_{21}H_{25}N_5O$ requires 363; found 364 $[M+H]^+$.

Example 1

(S)-4-(5-chloro-3-(5,6-dimethylnicotinamido)-2-methylbenzyl)-N-(cyclopropylmethyl)-2-methylpiperazine-1-carboxamide (E1)

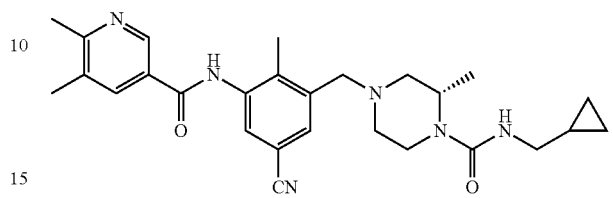

To a mixture of 5,6 dimethylnicotinic acid (D3, 51.7 mg), HATU (162 mg) and DIPEA (73.7 mg) in DMF (1.5 mL) was added (S)-4-(3-amino-5-chloro-2-methylbenzyl)-N-(cyclopropylmethyl)-2-methylpiperazine-1-carboxamide (D54, 100 mg). The mixture was stirred at 50° C. for 15 hours. The mixture was quenched with water, and extracted with EA (2×50 mL). The combined organic layers were dried over $Na_2SO_4$, and concentrated. The residue was purified by preparative HPLC to afford the title compound (30 mg) as white solid. $^1$H NMR (400 MHz, MeOD-$d_4$): 8.84 (d, J=1.2 Hz, 1H), 8.14 (d, J=1.2 Hz, 1H), 7.36 (d, J=2.0 Hz, 1H), 7.32 (d, J=2.0 Hz, 1H), 4.19 (brs, 1H), 3.74 (d, J=12.8 Hz, 1H), 3.52 (s, 2H), 3.10-3.02 (m, 3H), 2.83 (d, J=10.8 Hz, 1H), 2.71 (d, J=11.2 Hz, 1H), 2.61 (s, 3H), 2.44 (s, 3H), 2.32 (s, 3H), 2.26-2.22 (m, 1H), 2.10-2.05 (m, 1H), 1.25 (d, J=6.8 Hz, 3H), 1.03-0.99 (m, 114), 0.49-0.44 (m, 2H), 0.22-0.18 (m, 2H). MS (ESI): $C_{26}H_{34}ClN_5O_2$ requires 483; found 484 $[M+H]^+$.

Example 2-19

Examples 2-19 were prepared using a similar procedure to that described for Example 1, with the specified reaction solvent and base listed in the table.

E2: (S)-cyclopentyl 4-(5-chloro-2-methyl-3-(3-(methylsulfonyl)propanamido)benzyl)-2-methylpiperazine-1-carboxylate E3: (S)-cyclopropylmethyl 4-(5-chloro-2-methyl-3-(3-(methylsulfonyl)propanamido)benzyl)-2-methylpiperazine-1-carboxylate 0.0

E4: (S)-N-(5-chloro-2-methyl-3-((3-methyl-4-(pyrrolidine-1-carbonyl)piperazin-1-yl)methyl)phenyl)-6-methylnicotinamide E5: (S)-N-(5-chloro-2-methyl-3-((3-methyl-4-(pyrrolidine-1-carbonyl)piperazin-1-yl)methyl)phenyl)-2-methylpyrimidine-5-carboxamide E6: (S)-N-(5-chloro-2-methyl-3-((3-methyl-4-(pyrrolidine-1-carbonyl)piperazin-1-yl)methyl)phenyl)-4,4,4-trifluorobutanamide E7: (S)-N-(5-chloro-2-methyl-3-((3-methyl-4-(pyrrolidine-1-carbonyl)piperazin-1-yl)methyl)phenyl)-2-cyanoisonicotinamide E8: (S)-N-(5-chloro-2-methyl-3-((3-methyl-4-(pyrrolidine-1-carbonyl)piperazin-1-yl)methyl)phenyl)-6-cyanonicotinamide E9: (S)-N-(5-chloro-2-methyl-3-((3-methyl-4-(pyrrolidine-1-carbonyl)piperazin-1-yl)methyl)phenyl)-5-cyano-6-methylnicotinamide E10&E11: N-(5-chloro-2-methyl-3-(((S)-3-methyl-4-(pyrrolidine-1-carbonyl)piperazin-1-yl)methyl)phenyl)-2-

((1r,4S)-4-hydroxycyclohexyl)acetamide and N-(5-chloro-2-methyl-3-(((S)-3-methyl-4-(pyrrolidine-1-carbonyl)piperazin-1-yl)methyl)phenyl)-2-((1s,4R)-4-hydroxycyclohexyl)acetamide E12: (S)-N-(5-chloro-2-methyl-3-((3-methyl-4-(pyrrolidine-1-carbonyl)piperazin-1-yl)methyl)phenyl)-5,5,5-trifluoropentanamide E13: (S)-N-(5-chloro-2-methyl-3-((3-methyl-4-(pyrrolidine-1-carbonyl)piperazin-1-yl)methyl)phenyl)-2-ethylpyrimidine-S-carboxamide E14: (S)-N-(5-chloro-2-methyl-3-((3-methyl-4-(piperidine-1-carbonyl)piperazin-1-yl)methyl)phenyl)-2-cyanoisonicotinamide E15: (S)-N-(5-chloro-2-methyl-3-((3-methyl-4-(piperidine-1-carbonyl)piperazin-1-yl)methyl)phenyl)-6-cyanonicotinamide E16: (S)-N-(5-chloro-2-methyl-3-((3-methyl-4-(piperidine-1-carbonyl)piperazin-1-yl)methyl)phenyl)-4,4,4-trifluorobutanamide E17: (S)-N-(5-chloro-2-methyl-3-((3-methyl-4-(piperidine-1-carbonyl)piperazin-1-yl)methyl)phenyl)-2-methylpyrimidine-5-carboxamide E18: (S)-N-(5-chloro-2-methyl-3-((3-methyl-4-(3-methylazetidine-1-carbonyl)piperazin-1-yl)methyl)phenyl)-2-cyanoisonicotinamide E19: (S)-N-(5-chloro-2-methyl-3-((3-methyl-4-(3-methylazetidine-1-carbonyl)piperazin-1-yl)methyl)phenyl)-6-cyanonicotinamide

| | Structure | Solvent/base | Characterization |
|---|---|---|---|
| E2 | 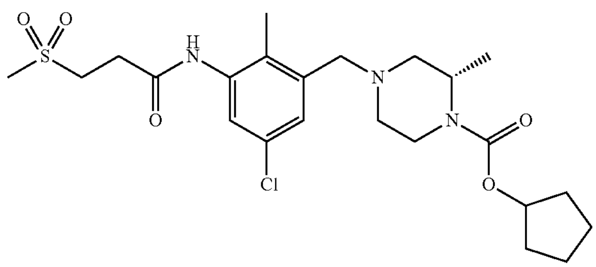 [SMILES: Cc1c(CN2CCN(C(=O)OC3CCCC3)[C@@H](C)C2)cc(Cl)cc1NC(=O)CCS(C)(=O)=O] | DMF/DIPEA | $^1$H NMR (400 MHz, MeOD-d$_4$): 7.26 (s, 1H), 7.10 (s, 1H), 4.96 (brs, 1H), 4.11 (brs, 1H), 3.70 (d, J = 12.7 Hz, 1H), 3.42 (t, J = 7.1 Hz, 2H), 3.21 (brs, 2H), 3.06-2.74 (m, 6H), 2.66 (d, J = 10.3 Hz, 1H), 2.54 (d, J = 11.3 Hz, 1H), 2.15 (s, 3H), 2.11-2.00 (m, 1H), 1.96-1.82 (m, 1H), 1.82-1.37 (m, 8H), 1.12 (d, J = 6.6 Hz, 3H). MS (ESI): C$_{23}$H$_{34}$ClN$_3$O$_5$S, requires 499; found 500 [M + H]$^+$. |
| E3 | 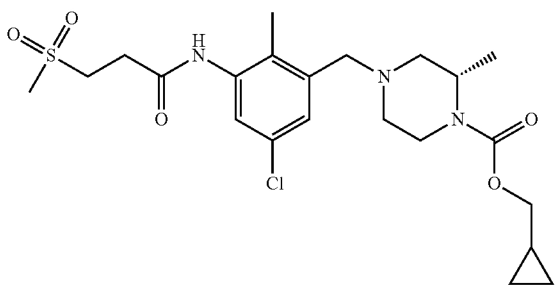 [SMILES: Cc1c(CN2CCN(C(=O)OCC3CC3)[C@@H](C)C2)cc(Cl)cc1NC(=O)CCS(C)(=O)=O] | DMF/DIPEA | $^1$H NMR (400 MHz, DMSO-d$_6$): 9.63 (s, 1H), 7.41 (s, 1H), 7.17 (s, 1H), 4.14 (brs, 1H), 3.92-3.64 (m, 3H), 3.49-3.37 (m, 4H), 3.10-2.92 (m, 4H), 2.85 (t, J = 7.3 Hz, 2H), 2.71 (d, J = 10.6 Hz, 1H), 2.59 (d, J = 11.1 Hz, 1H), 2.31-2.05 (m, 4H), 1.96 (t, J = 10.3 Hz, 1H), 1.26-0.94 (m, 4H), 0.48 (d, J = 6.7 Hz, 2H), 0.24 (d, J = 4.4 Hz, 2H). MS (ESI): C$_{22}$H$_{32}$ClN$_3$O$_5$S, requires 485; found 486 [M + H]$^+$. |
| E4 | 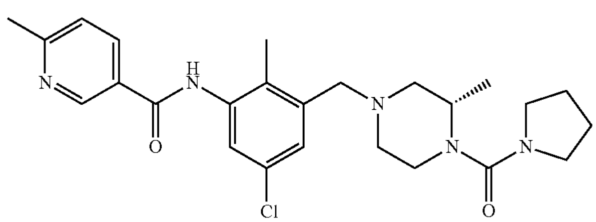 [SMILES: Cc1ccc(C(=O)Nc2cc(Cl)cc(CN3CCN(C(=O)N4CCCC4)[C@@H](C)C3)c2C)cn1] | DCM/DIPEA | $^1$H NMR (400 MHz, DMSO-d$_6$): 10.09 (s, 1H), 9.01 (d, J = 2.0 Hz, 1H), 8.20 (dd, J = 8.0 Hz, 2.4 Hz, 1H), 7.42 (d, J = 8.0 Hz, 1H), 7.38 (d, J = 2.0 Hz, 1H), 7.26 (d, J = 2.4 Hz, 1H), 3.89-3.85 (brs, 1H), 3.48-3.41 (m, 2H), 3.36 (brs, 1H), 3.25-3.22 (m, 4H), 3.04-2.97 (m, 1H), 2.67-2.56 (m, 5H), 2.21 (s, 3H), 2.18-2.03 (m, 2H), 1.75-1.71 (m, 4H), 1.18 (d, J = 6.4 Hz, 3H). MS (ESI): C$_{25}$H$_{32}$ClN$_5$O$_2$ requires 469; found 470 [M + H]$^+$. |
| E5 | 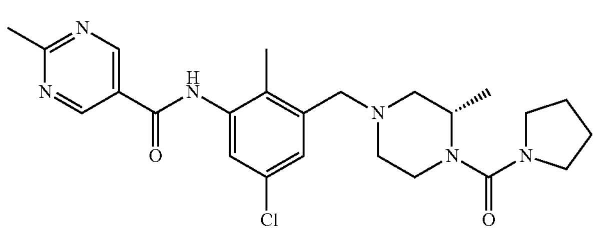 [SMILES: Cc1ncc(C(=O)Nc2cc(Cl)cc(CN3CCN(C(=O)N4CCCC4)[C@@H](C)C3)c2C)cn1] | DCM/DIPEA | $^1$H NMR (400 MHz, DMSO-d$_6$): 10.25 (brs, 1H), 9.18 (s, 2H), 7.42 (d, J = 2.0 Hz, 1H), 7.27 (d, J = 2.0 Hz, 1H), 3.86-3.85 (m, 1H), 3.48-3.40 (m, 2H), 3.36-3.32 (m, 1H), 3.25-3.22 (m, 4H), 3.04-2.97 (m, 1H), 2.72 (s, 3H), 2.64 (d, J = 10.8 Hz, 1H), 2.54 (d, J = 10.8 Hz, 1H), 2.23 (s, 3H), 2.19 (dd, J = 11.2, 3.5 Hz, 1H), 2.09-2.02 (m, 1H), 1.75-1.71 (m, 4H), 1.18 (d, J = 6.8 Hz, 3H). MS (ESI): C$_{24}$H$_{31}$ClN$_6$O$_2$ requires 470; found 471 [M + H]$^+$ |

| | Structure | Solvent/base | Characterization |
|---|---|---|---|
| E6 | 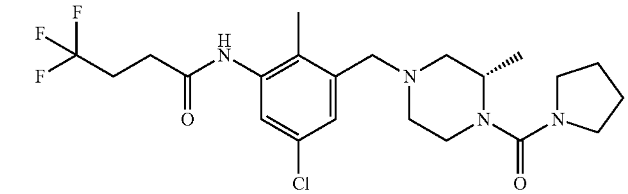 [SMILES: Cc1c(CN2CCN(C(=O)N3CCCC3)[C@@H](C)C2)cc(Cl)cc1NC(=O)CCC(F)(F)F] | DCM/DIPEA | $^1$H NMR (400 MHz, MeOD-$d_4$): 7.33 (d, J = 2.4 Hz, 1H), 7.21 (d, J = 2.0 Hz, 1H), 3.97-3.96 (m, 1H), 3.45-3.42 (m, 3H), 3.36-3.35 (m, 4H), 3.24-3.17 (m, 1H), 2.74-2.71 (m, 3H), 2.66-2.54 (m, 3H), 2.29-2.25 (m, 4H), 2.17-2.10 (m, 1H), 1.88-1.80 (m, 4H), 1.30 (d, J = 6.8 Hz, 3H). MS (ESI): $C_{22}H_{30}ClF_3N_4O_2$ requires 474; found 475 [M + H]$^+$. |
| E7 | 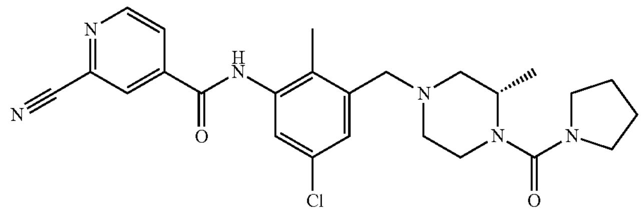 [SMILES: Cc1c(CN2CCN(C(=O)N3CCCC3)[C@@H](C)C2)cc(Cl)cc1NC(=O)c1ccnc(C#N)c1] | DCM/DIPEA | $^1$H NMR (400 MHz, MeOD-$d_4$): 8.92 (d, J = 4.8 Hz, 1H), 8.37 (s, 1H), 8.17 (dd, J = 4.8 Hz, 1.2 Hz, 1H), 7.38 (d, J = 2.0 Hz, 1H), 7.31 (d, J = 2.4 Hz, 1H), 3.98-3.97 (m, 1H), 3.50 (s, 2H), 3.45 (d, J = 13.2 Hz, 1H), 3.37-3.36 (m, 4H), 3.25-3.18 (m, 1H), 2.74 (d, J = 11.2 Hz, 1H), 2.63 (d, J = 11.2 Hz, 1H), 2.31-2.28 (m, 4H), 2.19-2.12 (m, 1H), 1.89-1.82 (m, 4H), 1.29 (d, J = 6.8 Hz, 3H). MS (ESI): $C_{25}H_{29}ClN_6O_2$ requires 480; found 481 [M + H]$^+$. |
| E8 | 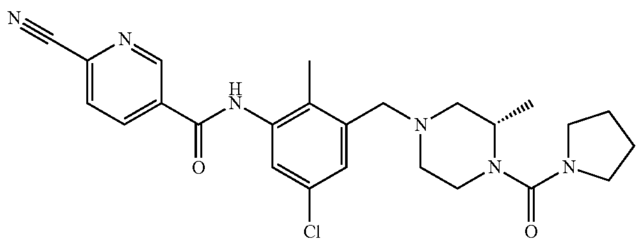 [SMILES: Cc1c(CN2CCN(C(=O)N3CCCC3)[C@@H](C)C2)cc(Cl)cc1NC(=O)c1ccc(C#N)nc1] | DCM/DIPEA | $^1$H NMR (400 MHz, MeOD-$d_4$): 9.25 (d, J = 1.6 Hz, 1H), 8.53 (dd, J = 8.0 Hz, 2.0 Hz, 1H), 8.07 (dd, J = 8.0, 0.8 Hz, 1H), 7.62 (s, 2H), 4.49 (brs, 2H), 3.41-3.28 (m, 11H), 2.37 (s, 3H), 1.90 (brs, 4H), 1.33 (d, J = 5.2 Hz, 3H). MS (ESI): $C_{25}H_{29}ClN_6O_2$ requires 480; found 481 [M + H]$^+$. |
| E9 | 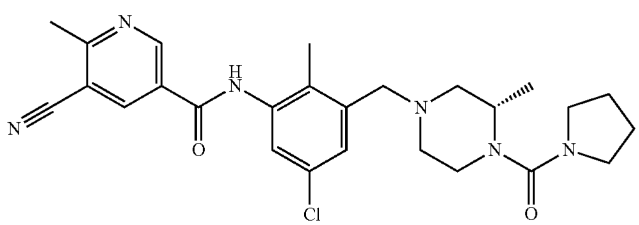 [SMILES: Cc1ncc(C(=O)Nc2cc(Cl)cc(CN3CCN(C(=O)N4CCCC4)[C@@H](C)C3)c2C)cc1C#N] | DCM/DIPEA | $^1$H NMR (400 MHz, MeOD-$d_4$): 9.22 (d, J = 2.0 Hz, 1H), 8.65 (d, J = 2.4 Hz, 1H), 7.60 (s, 2H), 4.45 (brs, 2H), 3.41-3.29 (m, 11H), 2.86 (s, 3H), 2.36 (s, 3H), 1.90 (brs, 4H), 1.33 (brs, 3H). MS (ESI): $C_{26}H_{31}ClN_6O_2$ requires 494; found 495 [M + H]$^+$. |
| E10 & E11 | | DMF/DIPEA | Isomer 1: $^1$H NMR (400 MHz, MeOD-$d_4$): 7.28 (d, J = 1.6 Hz, 1H), 7.21 (d, J = 1.2 Hz, 1H), 3.96-3.95 (m, 1H), 3.53-3.40 (m, 4H), 3.36-3.35 (m, 3H), 3.22-3.17 (m, 1H), 2.92-2.90 (m, 0.3H), 2.83-2.71 (m, 2H), 2.61-2.59 (m, 0.7H), 2.36-2.22 (m, 6H), 2.15-2.05 (m, 1H), 1.98-1.75 (m, 9H), 1.70-1.61 (m, 1H), 1.52-1.46 (m, 0.5H), 1.34-1.26 (m, 4H), 1.19-1.11 (m, 1.5H), 1.05 (d, J = 5.2 Hz, 1H). MS (ESI): $C_{26}H_{39}ClN_4O_3$ requires 490; found 491 [M + H]$^+$. Isomer 2: $^1$H NMR (400 MHz, DMSO-$d_6$): 9.37 (s, 1H), 7.37 (d, J = 1.2 Hz, 1H), 7.14 (s, 1H), 4.50 (d, J = 3.6 Hz, 1H), 3.84-3.83 (brs, 1H), 3.45-3.39 (m, 4H), 3.24-3.21 (m, 4H), 3.02-2.96 (m, 1H), 2.63-2.61 (m, 1H), 2.21-2.20 (m, 2H), 2.17-2.15 (m, 4H), 2.05-1.99 (m, 1H), 1.82-1.80 (m, 2H), 1.72-1.69 (m, 7H), 1.23-0.96 (m, 8H). MS (ESI): $C_{26}H_{39}ClN_4O_3$ requires 490; found 491 [M + H]$^+$. |

-continued

| | Structure | Solvent/base | Characterization |
|---|---|---|---|
| E12 | (structure) | DCM/DIPEA | ¹H NMR (400 MHz, MeOD-d₄): 7.33 (d, J = 2.0 Hz, 1H), 7.21 (d, J = 2.4 Hz, 1H), 3.97-3.95 (m, 1H), 3.45 (s, 2H), 2.43 (brs, 1H), 3.36-3.31 (m, 4H), 3.24-3.17 (m, 1H), 2.72 (d, J = 11.2 Hz, 1H), 2.61 (d, J = 11.2 Hz, 1H), 2.55 (t, J = 7.6 Hz, 2H), 2.32-2.16 (m, 6H), 2.16-2.10 (m, 1H), 2.00-1.92 (m, 2H), 1.88-1.82 (m, 4H), 1.27 (d, J = 6.4 Hz, 3H). 19$^F$ NMR (376 MHz, MeOD-d₄): −67.92. MS (ESI): $C_{23}H_{32}ClF_3N_4O_2$ requires 488; found 489 [M + H]⁺. |
| E13 | (structure) | DCM/DIPEA | ¹H NMR (400 MHz, MeOD-d₄): 9.23 (s, 2H), 7.40 (d, J = 2.4 Hz, 1H), 7.31 (d, J = 2.0 Hz, 1H), 3.99-3.97 (m, 1H), 3.50 (s, 2H), 3.45 (d, J = 13.2 Hz, 1H), 3.37-3.36 (m, 4H), 3.24-3.22 (m, 1H), 3.07 (q, J = 7.5 Hz, 2H), 2.75 (d, J = 10.0 Hz, 1H), 2.63 (d, J = 11.2 Hz, 1H), 2.32-2.28 (m, 4H), 2.18-2.15 (m, 1H), 1.86-1.85 (m, 4H), 1.40 (t, J = 8.0 Hz, 3H), 1.29 (d, J = 6.8 Hz, 3H). MS (ESI): $C_{25}H_{33}ClN_6O_2$ requires 484; found 485 [M + H]⁺. |
| E14 | (structure) | DCM/DIPEA | ¹H NMR (400 MHz, MeOD-d₄): 8.94 (d, J = 4.8 Hz, 1H), 8.37 (s, 1H), 8.16 (dd, J = 5.2 Hz, 1.6 Hz, 1H), 7.62-7.61 (m, 2H), 4.49 (s, 2H), 3.39-3.31 (m, 11H), 2.37 (s, 3H), 1.67-1.64 (m, 2H), 1.59-1.58 (m, 4H), 1.30 (d, J = 4.4 Hz, 3H). MS (ESI): $C_{26}H_{31}ClN_6O_2$ requires 494; found 495 [M + H]⁺. |
| E15 | (structure) | DCM/DIPEA | ¹H NMR (400 MHz, MeOD-d₄): 9.25 (d, J = 2.0 Hz, 1H), 8.53 (dd, J = 8.0 Hz, 1.6 Hz, 1H), 8.07 (d, J = 8.0 Hz, 1H), 7.62 (s, 2H), 4.50 (m, 2H), 3.48-3.31 (m, 11H), 2.37 (s, 3H), 1.67-1.64 (m, 2H), 1.59 (brs, 4H), 1.30 (d, J = 4.0 Hz, 3H). MS (ESI): $C_{26}H_{31}ClN_6O_2$ requires 494; found 495 [M + H]⁺. |
| E16 | (structure) | DCM/DIPEA | ¹H NMR (400 MeOD-d₄): 7.54 (d, J = 1.6 Hz, 1H), 7.51 (s, 1H), 4.43 (brs, 2H), 3.37-3.28 (m, 11H), 2.76 (t, J = 7.2 Hz, 2H), 2.67-2.57 (m, 2H), 2.31 (s, 3H), 1.68-1.64 (m, 2H), 1.59-1.58 (m, 4H), 1.28 (brs, 3H). MS (ESI): $C_{23}H_{32}ClF_3N_4O_2$ requires 488; found 489 [M + H]⁺. |
| E17 | (structure) | DCM/DIPEA | ¹H NMR (400 MHz, MeOD-d₄): 9.20 (s, 2H), 7.39 (d, J = 2.0 Hz, 1H), 7.31 (d, J = 2.0 Hz, 1H), 3.89-3.83 (m, 1H), 3.49 (s, 2H), 3.27-3.21 (m, 6H), 2.79 (s, 3H), 2.73 (d, J = 10.0 Hz, 1H), 2.61 (d, J = 10.8 Hz, 1H), 2.32-2.29 (m, 4H), 2.18-2.12 (m, 1H), 1.64-1.53 (m, 6H), 1.26 (d, J = 6.8 Hz, 3H). MS (ESI): $C_{25}H_{33}ClN_6O_2$ requires 484; found 485 [M + H]⁺. |

| | Structure | Solvent/base | Characterization |
|---|---|---|---|
| E18 | 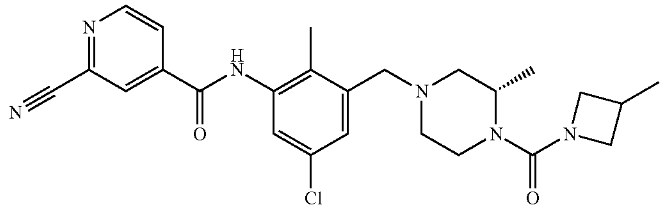 [SMILES: Cc1c(CN2CCN(C(=O)N3CC(C)C3)[C@@H](C)C2)cc(Cl)cc1NC(=O)c1ccnc(C#N)c1] | DCM/DIPEA | ¹H NMR (400 MHz, MeOD-d₄): 8.94 (dd, J = 5.2 Hz, 0.8 Hz, 1H), 8.37 (d, J = 0.8 Hz, 1H), 8.16 (dd, J = 5.2 Hz, 1.2 Hz, 1H), 7.59 (s, 2H), 4.38-4.31 (m, 3H), 4.19-4.14 (m, 2H), 3.89-3.85 (m, 1H), 3.64-3.60 (m, 2H), 3.34-3.31 (m, 3H), 3.20 (brs, 1H), 3.04 (brs, 1H), 2.72-2.71 (m, 1H), 2.35 (s, 3H), 1.35 (d, J = 6.8 Hz, 3H), 1.25 (d, J = 7.2 Hz, 3H). MS (ESI): $C_{25}H_{29}ClN_6O_2$ requires 480; found 481 [M + H]⁺. |
| E19 | 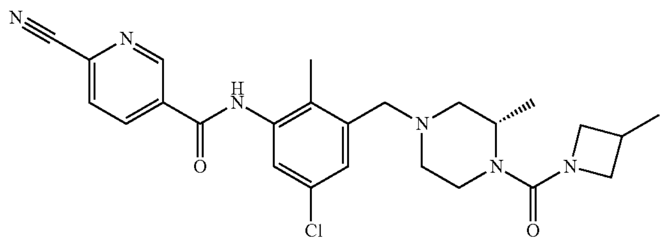 [SMILES: Cc1c(CN2CCN(C(=O)N3CC(C)C3)[C@@H](C)C2)cc(Cl)cc1NC(=O)c1ccc(C#N)nc1] | DCM/DIPEA | ¹H NMR (400 MHz, MeOD-d₄): 9.25 (d, J = 1.6 Hz, 1H), 8.53 (dd, J = 8.0 Hz, 2.4 Hz, 1H), 8.07 (dd, J = 8.0 Hz, 0.8 Hz, 1H), 7.61 (s, 2H), 4.44 (s, 2H), 4.32 (brs, 1H), 4.19-3.86 (m, 2H), 3.87 (d, J = 12.8 Hz, 1H), 3.64-3.60 (m, 2H), 3.44-3.25 (m, 4H), 3.14-3.10 (m, 1H), 2.76-2.67 (m, 1H), 2.36 (s, 3H), 1.36 (d, J = 7.2 Hz, 3H), 1.24 (d, J = 6.8 Hz, 3H). MS (ESI): $C_{25}H_{29}ClN_6O_2$ requires 480; found 481 [M + H]⁺. |

Example 20

(S)-N-(5-chloro-2-methyl-3-((3-methyl-4-(piperidine-1-carbonyl)piperazin-1-yl)methyl)phenyl)-2-(3,3-difluorocyclobutyl)acetamide, trifluoroacetic acid salt (E20)

Example 21

(S)-4-(5-chloro-3-(6-ethylnicotinamido)-2-methylbenzyl)-N-(cyclopropylmethyl)-2-methylpiperazine-1-carboxamide (E21)

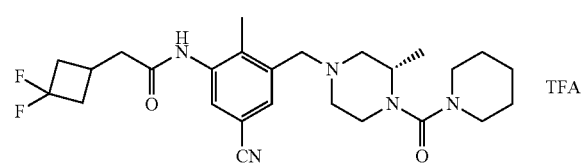 [SMILES: Cc1c(CN2CCN(C(=O)N3CCCCC3)[C@@H](C)C2)cc(C#N)cc1NC(=O)CC1CC(F)(F)C1]

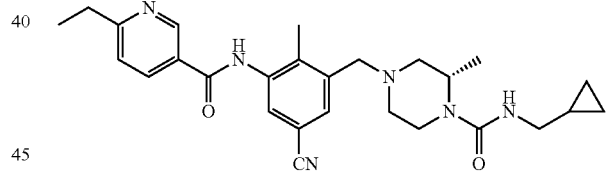

A mixture of (S)-(4-(3-amino-5-chloro-2-methylbenzyl)-2-methylpiperazin-1-yl)(piperidin-1-yl)methanone (D56, 97 mg), 2-(3,3-difluorocyclobutyl)acetic acid (D13, 40 mg), EDC (77 mg) and DIPEA (0.093 mL) in DMF (5 mL) was stirred for 16 hours. Cold water (30 mL) was added and the aqueous layer was extracted with DCM (2×30 mL). The combined organic layers were dried over Na₂SO₄, filtered and concentrated in vacuo. The residue was purified by column chromatography (eluting with EA:PE=50% to 100%) and preparative HPLC to afford the title compound (10 mg) as white solid. ¹H NMR (400 MHz, MeOD-d₄): 7.45 (brs, 2H), 4.39-4.38 (m, 2H), 3.38-3.22 (m, 11H), 2.77-2.75 (m, 2H), 2.70-2.67 (m, 2H), 2.62-2.60 (m, 1H), 2.43-2.32 (m, 2H), 2.28 (s, 3H), 1.67-1.57 (m, 6H), 1.28-1.24 (m, 3H). ¹⁹F NMR (376 MHz, MeOD-d₄): −77.13, −84.44, −96.75. MS (ESI): $C_{25}H_{35}ClF_2N_4O_2$ requires 496; found 497 [M+H]⁺.

A mixture of 6-ethylnicotinic acid (D15, 43.1 mg), (S)-4-(3-amino-5-chloro-2-methylbenzyl)-N-(cyclopropylmethyl)-2-methylpiperazine-1-carboxamide (D54, 100 mg), EDC (82 mg) and HOBT (65.5 mg) and in DMF (5 mL) was stirred at 25° C. for 2 days. Cold water (30 mL) was added and the aqueous layer was extracted with DCM (2×100 mL). The combined organic layers were dried over Na₂SO₄, filtered and concentrated in vacuo. The resulting residue was purified by preparative HPLC to afford the title compound (20 mg) as white solid. ¹H NMR (400 MHz, MeOD-d₄): 9.02 (d, J=2.4 Hz, 1H), 8.30 (dd, J=8.0 Hz, 2.0 Hz, 1H), 7.48 (d, J=8.0 Hz, 1H), 7.35 (d, J=2.0 Hz, 1H), 7.30 (d, J=2.0 Hz, 1H), 4.17 (brs, 1H), 3.72 (d, J=12.8 Hz, 1H), 3.50 (s, 2H), 3.12-2.97 (m, 3H), 2.94-2.89 (m, 2H), 2.81 (d, J=10.8 Hz, 1H), 2.69 (d, J=11.2 Hz, 1H), 2.31 (s, 3H), 2.25-2.21 (m, 1H), 2.09-2.02 (m, 1H), 1.34 (t, J=7.6 Hz, 3H), 1.23 (d, J=6.4 Hz, 3H), 1.04-0.95 (m, 1H), 0.47-0.42 (m, 2H), 0.21-0.17 (m, 2H). MS (ESI): $C_{26}H_{34}ClN_5O_2$ requires 483; found 484 [M+H]⁺.

Example 22

(S)-4-(5-chloro-3-(5-chloronicotinamido)-2-methylbenzyl)-N-(cyclopropylmethyl)-2-methylpiperazine-1-carboxamide (E22)

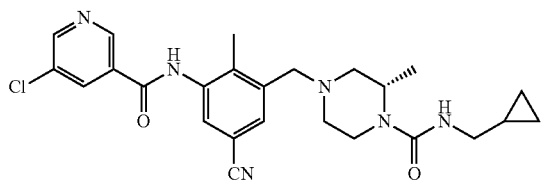 [SMILES: Cc1c(CN2CCN(C(=O)NCC3CC3)[C@@H](C)C2)cc(C#N)cc1NC(=O)c1cncc(Cl)c1]

A mixture of 5-chloronicotinic acid (22.45 mg) and sulfurous dichloride (1 mL) was stirred for 5 hours at 60° C. After cooling to RT, the mixture was concentrated under reduced pressure to dryness. The residue was redissolved in DCM (10 mL) which was added slowly to the mixture of (S)-4-(3-amino-5-chloro-2-methylbenzyl)-N-(cyclopropylmethyl)-2-methylpiperazine-1-carboxamide (D54, 50 mg) and DIPEA (5 mL) in DCM (10 mL) at 0° C. The mixture was stirred at RT for 2 hours, and then washed with water. The organic layer was dried over $Na_2SO_4$, filtered and concentrated to give the crude product which was purified by preparative HPLC to afford the title compound (30 mg) as white solid. $^1$H NMR (400 MHz, CDCl$_3$): 9.07 (s, 1H), 8.74 (brs, 2H), 8.33 (s, 1H), 7.59 (s, 1H), 7.18 (s, 1H), 4.52-4.49 (m, 1H), 3.93 (brs, 1H), 3.52 (d, J=12.4 Hz, 1H), 3.44 (d, J=13.2 Hz, 1H), 3.34 (d, J=12.8 Hz, 1H), 3.08-3.05 (m, 2H), 2.96-2.89 (m, 1H), 2.58-2.55 (m, 2H), 2.28 (s, 3H), 2.21-2.18 (m, 1H), 1.94-1.87 (in, 1H), 1.17 (d, J=6.8 Hz, 3H), 0.93-0.90 (m, 2H), 0.51-0.46 (m, 2H), 0.17 (d, J=4.8 Hz, 2H). MS (ESI: $C_{24}H_{29}Cl_2N_5O_2$ requires 489; found 490 [M+H]$^+$.

Example 23

(S)-4-(5-chloro-3-(5-fluoro-6-methylnicotinamido)-2-methylbenzyl)-N-(cyclopropylmethyl)-2-methylpiperazine-1-carboxamide (E23)

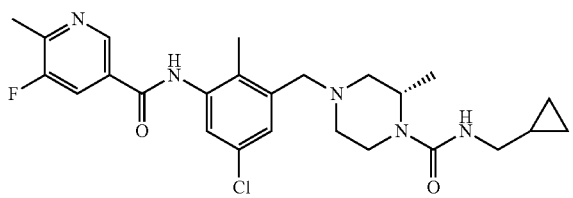 [SMILES: Cc1ncc(C(=O)Nc2cc(Cl)cc(CN3CCN(C(=O)NCC4CC4)[C@@H](C)C3)c2C)cc1F]

To a mixture of 5-fluoro-6-methylnicotinic acid (D19, 44.2 mg) in DCM (10 mL) were added oxalyl dichloride (109 mg) and two drops of DMF. The reaction was stirred for 5 hours at 0° C. Then the mixture was concentrated to dryness under reduced pressure. The residue was redissolved in DCM (10 mL), which was slowly added to a mixture of (S)-4-(3-amino-5-chloro-2-methylbenzyl)-N-(cyclopropylmethyl)-2-methylpiperazine-1-carboxamide (D54, 100 mg) and DIPEA (5 mL) in DCM (10 mL) at 0° C. The reaction mixture was allowed to warm to RT and stirred for 2 hours. The mixture was washed with water (15 mL). The organic layer was dried over $Na_2SO_4$, filtered and concentrated in vacuo to give the crude product, which was purified by preparative HPLC to afford the title compound (24 mg) as white solid. $^1$H NMR (400 MHz, CDCl$_3$): 8.82 (s, 1H), 7.97 (s, 1H), 7.92 (dd, J=8.8 Hz, 1.2 Hz, 1H), 7.79 (s, 1H), 7.18 (d, J=2.0 Hz, 1H), 4.47 (t, J=5.2 Hz, 1H), 4.03 (brs, 1H), 3.64 (d, J=12.0 Hz, 1H), 3.46-3.38 (m, 2H), 3.11-3.02 (m, 3H), 2.70 (d, J=11.2 Hz, 1H), 2.63 (d, J=3.2 Hz, 3H), 2.60-2.56 (m, 1H), 2.32 (s, 3H), 2.26-2.22 (m, 1H), 2.05-2.00 (m, 1H), 1.22 (d, J=6.4 Hz, 3H), 0.98-0.95 (m, 1H), 0.50-0.47 (m, 2H), 0.19-0.17 (m, 2H). MS (ESI): $C_{23}H_{31}ClFN_5O_2$ requires 487; found 488 [M+H]$^+$.

Example 24

(S)-4-(5-chloro-3-(3-cyanobenzamido)-2-methylbenzyl)-N-(cyclopropylmethyl)-2-methylpiperazine-1-carboxamide, trifluoroacetic acid salt (E24)

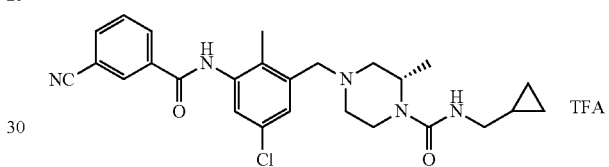

To a solution of (S)-4-(3-amino-5-chloro-2-methylbenzyl)-N-(cyclopropylmethyl)-2-methylpiperazine-1-carboxamide (D54, 80 mg) in DCM (10 mL) added 3-cyanobenzoyl chloride (37.8 mg) and DIPEA (0.119 mL). After stirring for 4 hours, the mixture was concentrated to give a yellow oil, which was purified by preparative HPLC to afford the title compound (80 mg) as a white solid. $^1$H NMR (400 MHz, DMSO-d$_6$): 10.32 (brs, 1H), 9.38 (brs, 1H), 8.41 (s, 1H), 8.27 (d, J=7.6 Hz, 1H), 8.11 (d, J=7.6 Hz, 1H), 7.78 (t, J=8.0 Hz, 1H), 7.65-7.60 (m, 2H), 6.78 (brs, 1H), 4.47 (brs, 2H), 4.02-3.96 (m, 1H), 3.31 (brs, 2H), 3.10 (brs, 2H), 2.95-2.87 (m, 2H), 2.21 (s, 3H), 1.20 (brs, 3H), 0.95-0.88 (m, 1H), 0.39-0.33 (m, 2H), 0.23-0.16 (m, 2H). $^{19}$F NMR (376 MHz, DMSO-d$_6$): -74.3. MS (ESI): $C_{26}H_{30}ClN_5O_2$ requires 479; found 480 [M+H]$^+$

Example 25

(S)-N-(5-chloro-2-methyl-3-((3-methyl-4-(pyrrolidine-1-carbonyl)piperazin-1-yl)methyl)phenyl)-3-cyanobenzamide (E25)

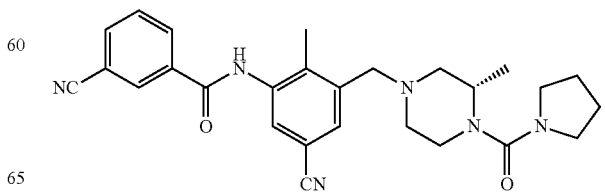

To a solution of (S)-(4-(3-amino-5-chloro-2-methylbenzyl)-2-methylpiperazin-1-yl)(pyrrolidin-1-yl)methanone (D55, 160 mg) and DMAP (167 mg) in DCM (30 mL) was added 3-cyanobenzoyl chloride (151 mg). The mixture was stirred at 40° C. overnight. After cooling to RT, the mixture was concentrated and the resulting residue was purified by preparative HPLC to afford the title compound (20 mg). $^1$H NMR (400 MHz, CDCl$_3$): 8.52 (s, 1H), 8.28 (s, 1H), 8.21 (d, J=7.6 Hz, 1H), 7.89 (d, J=8.0 Hz, 1H), 7.80-7.78 (m, 1H), 7.68 (t, J=8.0 Hz, 1H), 7.29-7.28 (m, 1H), 4.23 (d, J=14.0 Hz, 1H), 4.12 (d, J=13.6 Hz, 1H), 3.67-3.64 (m, 1H), 3.52-3.47 (m, 1H), 3.36 (brs, 5H), 3.25-3.22 (m, 1H), 3.05-2.98 (m, 2H), 2.31 (s, 3H), 1.88-1.87 (m, 4H), 1.42 (d, J=6.8 Hz, 3H). MS (ESI): C$_{26}$H$_{30}$ClN$_5$O$_2$ requires 479; found 480 [M+H]$^+$.

Example 26

(S)-N-(5-fluoro-2-methyl-3-((3-methyl-4-(pyrrolidine-1-carbonyl)piperazin-1-yl)methyl)phenyl)-6-methylnicotinamide (E26)

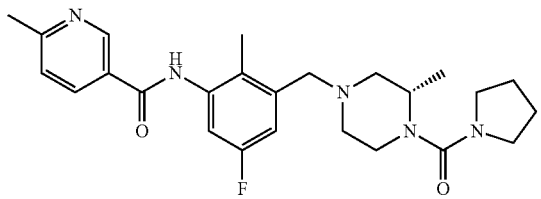 [SMILES: Cc1ccc(C(=O)Nc2cc(F)cc(CN3CCN(C(=O)N4CCCC4)[C@@H](C)C3)c2C)cn1]

Example 26 was prepared using a similar procedure to that described for Example 25. $^1$H NMR (400 MHz, MeOD-d$_4$): 9.01 (s, 1H), 8.29 (dd, J=8.4 Hz, 2.4 Hz, 1H), 7.49 (d, J=8.0 Hz, 1H), 7.13-7.07 (m, 2H), 3.99-3.97 (m, 1H), 3.50 (s, 2H), 3.45 (d, J=13.2 Hz, 1H), 3.37 (brs, 4H), 3.26-3.19 (m, 1H), 2.76 (d, J=10.4 Hz, 1H), 2.67-2.64 (m, 4H), 2.32-2.29 (m, 4H), 2.19-2.12 (m, 1H), 1.86-1.85 (m, 4H), 1.30 (d, J=6.8 Hz, 3H). MS (ESI): C$_{25}$H$_{32}$FN$_5$O$_2$ requires 453; found 454 [M+H]$^+$.

Example 27

(2S)-4-(3-(2-(1-acetylpyrrolidin-3-yl)acetamido)-5-chloro-2-methylbenzyl)-N-(cyclopropylmethyl)-2-methylpiperazine-1-carboxamide, trifluoroacetic acid salt (E27)

To a solution of TEA (0.030 mL) and (2S)-4-(5-chloro-2-methyl-3-(2-(pyrrolidin-3-yl)acetamido)benzyl)-N-(cyclopropylmethyl)-2-methylpiperazine-1-carboxamide, 2 hydrochloric acid salt (D61, 100 mg) in DCM (10 mL) was added acetyl chloride (16.99 mg) at 0° C. The mixture was stirred at this temperature for 30 mins. Cold water (30 mL) was added and the resulting mixture was neutralized with sat. NaHCO$_3$ solution. The aqueous layer was extracted with DCM (2×100 mL). The combined organic layers were dried over Na$_2$SO$_4$, filtered and concentrated in vacuo. The residue was purified by preparative HPLC to afford the title compound (20 mg). $^1$H NMR (400 MHz, MeOD-d$_4$): 7.55-7.53 (m, 2H), 4.52-4.42 (m, 3H), 4.09 (d, J=14.4 Hz, 1H), 3.83-3.35 (m, 5.5H), 3.29-3.24 (m, 2H), 3.16-2.98 (m, 3.5H), 2.80-2.52 (m, 3H), 2.30-2.13 (m, 4H), 2.06 (d, 3H), 1.86-1.65 (m, 1H), 1.30 (d, J=6.8 Hz, 3H), 1.05-0.95 (m, 1H), 0.48-0.44 (m, 2H), 0.21-0.18 (m, 2H). $^{19}$F NMR (376 MHz, MeOD-d$_4$): −77.28. MS (ESI): C$_{26}$H$_{38}$ClN$_5$O$_3$ requires 503; found 504 [M+H]$^+$.

Example 28

(2S)-4-(3-(2-(1-acetylpyrrolidin-2-yl)acetamido)-5-chloro-2-methylbenzyl)-N-(cyclopropylmethyl)-2-methylpiperazine-1-carboxamide (E28)

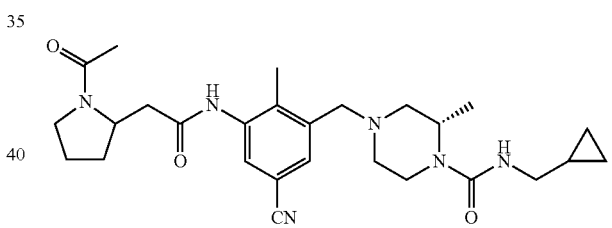

Example 28 was prepared using a similar procedure to that described for Example 27. $^1$H NMR (400 MHz, MeOD-d$_4$): 7.57 (d, J=2.4 Hz, 1H), 7.52 (s, 1H), 4.49-4.40 (m, 4H), 4.10-4.07 (m, 1H), 3.65-3.38 (m, 4.5H), 3.28-3.21 (m, 1.5H), 3.09-2.96 (m, 4H), 2.52-2.46 (m, 1H), 2.31 (d, J=2.8 Hz, 3H), 2.13-1.92 (m, 7H), 1.31 (d, J=7.2 Hz, 3H), 1.06-0.96 (m, 1H), 0.50-0.45 (m, 2H), 0.23-0.19 (m, 2H). MS (ESI): C$_{26}$H$_{38}$ClN$_5$O$_3$ requires 503; found 504 [M+H]$^+$.

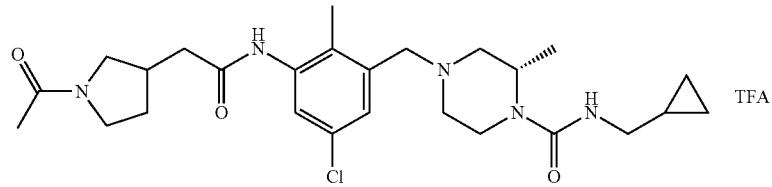 [SMILES: CC(=O)N1CCC(CC(=O)Nc2cc(Cl)cc(CN3CCN(C(=O)NCC4CC4)[C@@H](C)C3)c2C)C1]

Example 29

(S)-4-(5-chloro-2-methyl-3-(6-methylnicotinamido)benzyl)-N-cyclopentyl-2-methylpiperazine-1-carboxamide (E29)

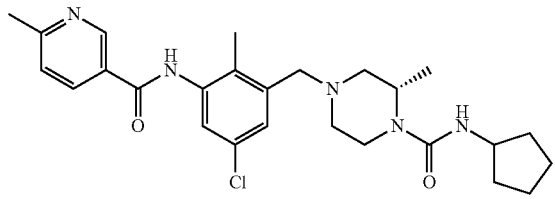 [SMILES: Cc1ccc(C(=O)Nc2cc(Cl)cc(CN3CCN(C(=O)NC4CCCC4)[C@@H](C)C3)c2C)cn1]

To a solution of (S)-N-(5-chloro-2-methyl-3-((3-methylpiperazin-1-yl)methyl)phenyl)-6-methylnicotinamide, 2 hydrochloric acid salt (D69, 100 mg), triphosgene (39.8 mg) in DCM (15 mL) was added DIPEA (0.281 mL). The mixture was stirred for 1 hour. Then cyclopentanamine (22.83 mg) was added into the above mixture. The mixture was stirred for an additional 2 hours. Cold water (30 mL) was added and the aqueous layer was extracted with DCM (2×30 mL). The combined organic layers were dried over $Na_2SO_4$, filtered and concentrated in vacuo. The residue was purified by column chromatography (eluting with EA:PE=50% to 100%) and preparative HPLC to afford the title compound (15 mg). $^1$H NMR (400 MHz, MeOD-$d_4$): 9.00 (d, J=1.2 Hz, 1H), 8.29 (dd, J=8.0 Hz, 2.0 Hz, 1H), 7.48 (d, J=8.0 Hz, 1H), 7.36 (d, J=2.4 Hz, 1H), 7.31 (d, J=2.0 Hz, 1H), 4.18 (brs, 1H), 4.06-4.00 (m, 1H), 3.71 (d, J=11.6 Hz, 1H), 3.50 (s, 2H), 3.11-3.04 (m, 1H), 2.80 (d, J=11.2 Hz, 1H), 2.69 (d, J=11.2 Hz, 1H), 2.64 (s, 3H), 2.30 (s, 3H), 2.24-2.20 (m, 1H), 2.08-2.01 (m, 1H), 1.96-1.88 (m, 2H), 1.75-1.66 (m, 2H), 1.62-1.52 (m, 2H), 1.48-1.39 (m, 2H), 1.21 (d, J=6.8 Hz, 3H). MS (ESI): $C_{26}H_{34}ClN_5O_2$ requires 483; found 484 [M+H]$^+$.

Example 30

(S)-N-(5-chloro-2-methyl-3-((3-methyl-4-(piperidine-1-carbonyl)piperazin-1-yl)methyl)phenyl)-6-methylnicotinamide (E30)

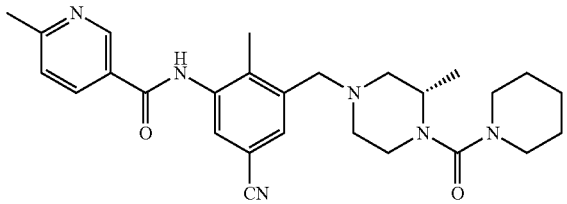 [SMILES: Cc1ccc(C(=O)Nc2cc(C#N)cc(CN3CCN(C(=O)N4CCCCC4)[C@@H](C)C3)c2C)cn1]

A mixture of (S)-N-(5-chloro-2-methyl-3-((3-methylpiperazin-1-yl)methyl)phenyl)-6-methylnicotinamide, 2 hydrochloric acid salt (D69, 150 mg), TEA (0.280 mL) and triphosgene (95 mg) in DCM (20 mL) was stirred at 0° C. for 30 minutes. After piperidine (34.3 mg) was added, the mixture was stirred at RT for 2 hours. The mixture was concentrated in vacuo and the crude product was purified by preparative HPLC to afford the title compound (52 mg) as white solid. $^1$H NMR (400 MHz, MeOD-$d_4$): 9.02 (d, J=1.6 Hz, 1H), 8.29 (dd, J=8.0 Hz, 2.4 Hz, 1H), 7.49 (d, J=8.0 Hz, 1H), 7.37 (d, J=2.4 Hz, 1H), 7.32 (d, J=2.4 Hz, 1H), 3.89-3.88 (m, 1H), 3.51 (s, 2H), 3.34-3.21 (m, 6H), 2.74 (d, J=10.4 Hz, 1H), 2.65-2.61 (m, 4H), 2.31-2.32 (m, 4H), 2.17-2.15 (m, 1H), 1.64-1.56 (m, 6H), 1.28 (d, J=6.8 Hz, 3H). MS (ESI): $C_{26}H_{34}ClN_5O_2$ requires 483; found 484 [M+H]$^+$.

Example 31-43

Examples 31-43 were prepared using a similar procedure to that described for Example 30, with the specified reaction solvent and base listed in the table.

E31: (S)-N-(5-chloro-2-methyl-3-((3-methyl-4-(3-methylazetidine-1-carbonyl)piperazin-1-yl)methyl)phenyl)-6-methylnicotinamide E32: (S)-N-(3-((4-(azetidine-1-carbonyl)-3-methylpiperazin-1-yl)methyl)-5-chloro-2-methylphenyl)-6-methylnicotinamide E33: (S)-4-(5-chloro-2-methyl-3-(6-methylnicotinamido)benzyl)-2-methyl-N-(3-methylcyclobutyl)piperazine-1-carboxamide E34: (S)-4-(5-chloro-2-methyl-3-(6-methylnicotinamido)benzyl)-N-(cyclopropylmethyl)-2-methylpiperazine-1-carboxamide E35: (S)-4-(5-chloro-2-methyl-3-(6-methylnicotinamido)benzyl)-N-(cyclobutylmethyl)-2-methylpiperazine-1-carboxamide E36: (S)-4-(5-chloro-2-methyl-3-(6-methylnicotinamido)benzyl)-N-(cyclopropylmethyl)-N,2-dimethylpiperazine-1-carboxamide E37: (S)-4-(5-chloro-2-methyl-3-(6-methylnicotinamido)benzyl)-N-(cyclobutylmethyl)-N,2-dimethylpiperazine-1-carboxamide E38: (S)-4-(5-chloro-2-methyl-3-(6-methylnicotinamido)benzyl)-N-isopropyl-2-methylpiperazine-1-carboxamide E39: (S)-4-(5-chloro-2-methyl-3-(6-methylnicotinamido)benzyl)-N-isobutyl-2-methylpiperazine-1-carboxamide E40: (S)-4-(5-chloro-2-methyl-3-(6-methylnicotinamido)benzyl)-N-cyclobutyl-2-methylpiperazine-1-carboxamide E41: (S)-N-(tert-butyl)-4-(5-chloro-2-methyl-3-(6-methylnicotinamido)benzyl)-2-methylpiperazine-1-carboxamide E42: (S)-N-(5-chloro-2-methyl-3-((3-methyl-4-(pyrrolidine-1-carbonyl)piperazin-1-yl)methyl)phenyl)-5-fluoro-6-methylnicotinamide E43: (S)-4-(5-chloro-3-(5-methoxy-6-methylnicotinamido)-2-methylbenzyl)-N-(cyclopropylmethyl)-2-methylpiperazine-1-carboxamide

| | Structure | Solvent/base | Characterization |
|---|---|---|---|
| E31 | 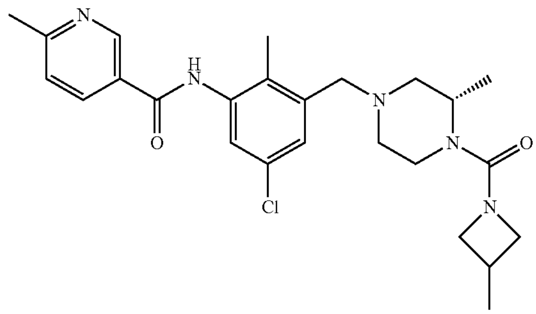 [SMILES: Cc1ccc(C(=O)Nc2cc(Cl)cc(CN3CCN(C(=O)N4CC(C)C4)[C@@H](C)C3)c2C)cn1] | DCM/DIPEA | $^1$H NMR (400 MHz, MeOD-d$_4$): 9.01 (s, 1H), 8.27 (d, J = 6.8 Hz, 1H), 7.47 (d, J = 8.0 Hz, 1H), 7.35 (s, 1H), 7.30 (s, 1H), 4.05-4.14 (m, 3H), 3.59-3.54 (m, 3H), 3.48 (s, 2H), 3.15 (t, J = 11.2 Hz, 1H), 2.77 (d, J = 10.8 Hz, 1H), 2.68-2.64 (m, 5H), 2.30 (s, 3H), 2.23-2.20 (m, 1H), 2.08-2.03 (m, 1H), 1.28-1.22 (m, 6H). MS (ESI): C$_{25}$H$_{32}$ClN$_5$O$_2$ requires 469; found 470 [M + H]$^+$. |
| E32 | 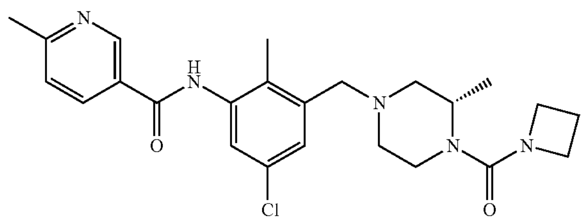 [SMILES: Cc1ccc(C(=O)Nc2cc(Cl)cc(CN3CCN(C(=O)N4CCC4)[C@@H](C)C3)c2C)cn1] | DCM/TEA | $^1$H NMR (400 MHz, MeOD-d$_4$): 9.01 (d, J = 2.0 Hz, 1H), 8.28 (dd, J = 8.0 Hz, 2.0 Hz, 1H), 7.49 (d, J = 8.0 Hz, 1H), 7.36 (d, J = 2.0 Hz, 1H), 7.30 (d, J = 2.4 Hz, 1H), 4.06-4.01 (m, 5H), 3.59 (d, J = 13.2 Hz, 1H), 3.49 (s, 2H), 3.19-3.12 (m, 1H), 2.78 (d, J = 10.8 Hz, 1H), 2.69-2.64 (m, 4H), 2.30-2.20 (m, 6H), 2.09-2.02 (m, 1H), 1.28 (d, J = 6.8 Hz, 3H). MS (ESI): C$_{24}$H$_{30}$ClN$_5$O$_2$ requires 455; found 456 [M + H]$^+$. |
| E33 | 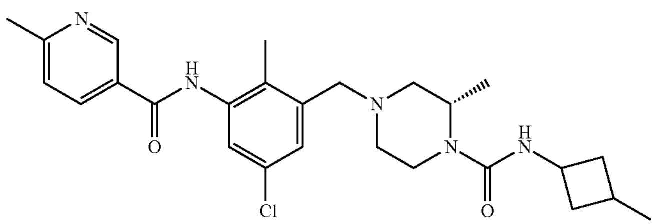 | DCM/DIPEA | $^1$H NMR (400 MHz, MeOD-d$_4$): 9.01 (d, J = 1.6 Hz, 1H), 8.28 (dd, J = 8.0 Hz, 1.6 Hz, 1H), 7.47 (d, J = 8.0 Hz, 1H), 7.35 (d, J = 1.6 Hz, 1H), 7.30 (d, J = 1.6 Hz, 1H), 4.36-4.28 (m, 0.5H), 4.17 (brs, 1H), 4.03-3.95 (m, 0.5H), 3.70 (d, J = 12.8 Hz, 1H), 3.48 (s, 2H), 3.09-3.03 (m, 1H), 2.79 (d, J = 10.4 Hz, 1H), 2.68 (d, J = 11.6 Hz, 1H), 2.64 (s, 3H), 2.44-2.38 (m, 1.5H), 2.30 (s, 3H), 2.20-2.18 (m, 1H), 2.15-1.90 (m, 3H), 1.55-1.47 (m, 1.5H), 1.21 (d, J = 6.8 Hz, 3H), 1.15 (d, J = 7.2 Hz, 1H), 1.07 (d, J = 6.4 Hz, 2H). MS (ESI): C$_{26}$H$_{34}$ClN$_5$O$_2$ requires 483; found 484.1 [M + H]$^+$. |
| E34 | 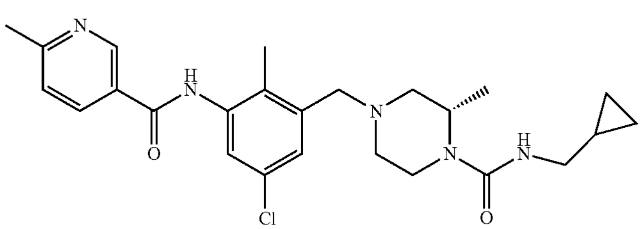 [SMILES: Cc1ccc(C(=O)Nc2cc(Cl)cc(CN3CCN(C(=O)NCC4CC4)[C@@H](C)C3)c2C)cn1] | DCM/TEA | $^1$H NMR (400 MHz, MeOD-d$_4$): 9.02 (d, J = 2.4 Hz, 1H), 8.29 (dd, J = 8.0 Hz, 2.0 Hz, 1H), 7.48 (d, J = 8.0 Hz, 1H), 7.37 (d, J = 2.4 Hz, 1H), 7.32 (s, 1H), 4.18 (brs, 1H), 3.74 (d, J = 12.8 Hz, 1H), 3.51 (s, 2H), 3.34-3.32 (m, 1H), 3.13-2.99 (m, 2H), 2.82 (d, J = 10.4 Hz, 1H), 2.70 (d, J = 10.8 Hz, 1H), 2.65 (s, 3H), 2.32 (s, 3H), 2.56-2.22 (m, 1H), 2.10-2.04 (m, 1H), 1.24 (d, J = 6.8 Hz, 3H), 1.03-0.95 (m, 1H), 0.45-0.40 (m, 2H), 0.18-0.15 (m, 2H). MS (ESI): C$_{25}$H$_{32}$ClN$_5$O$_2$ requires 469; found 470 [M + H]$^+$. |
| E35 | 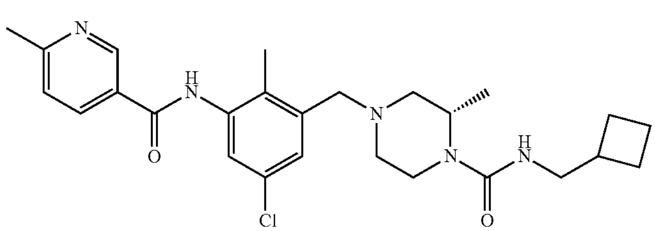 [SMILES: Cc1ccc(C(=O)Nc2cc(Cl)cc(CN3CCN(C(=O)NCC4CCC4)[C@@H](C)C3)c2C)cn1] | DCM/TEA | $^1$H NMR (400 MHz, MeOD-d$_4$): 9.02 (s, 1H), 8.30-8.28 (m, 1H), 7.49 (d, J = 8.4 Hz, 1H), 7.36 (d, J = 2.4 Hz, 1H), 7.32 (s, 1H), 4.15 (brs, 1H), 3.72 (d, J = 12.8 Hz, 1H), 3.51 (s, 2H), 3.37-3.33 (m, 1H), 3.23-3.08 (m, 2H), 2.82 (d, J = 10.0 Hz, 1H), 2.72-2.65 (m, 4H), 2.53-2.49 (m, 1H), 2.32 (s, 3H), 2.25-2.22 (m, 1H), 2.09-2.00 (m, 3H), 1.92-1.86 (m, 2H), 1.76-1.69 (m, 2H), 1.23 (d, J = 6.8 Hz, 3H). MS (ESI): C$_{26}$H$_{34}$ClN$_5$O$_2$ requires 483; found 484 [M + H]$^+$. |

-continued

| | Structure | Solvent/base | Characterization |
|---|---|---|---|
| E36 | 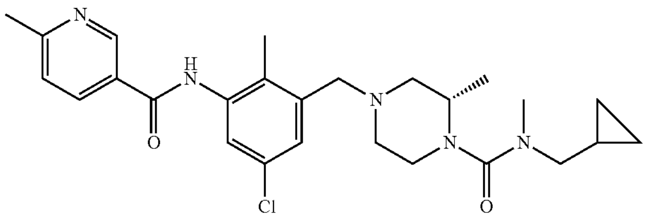 [SMILES: Cc1ccc(C(=O)Nc2cc(Cl)cc(CN3CCN(C(=O)N(C)CC4CC4)[C@@H](C)C3)c2C)cn1] | DCM/DIPEA | ¹H NMR (400 MHz, MeOD-d₄): 9.00 (s, 1H), 8.27 (dd, J = 8.4 Hz, 2.0 Hz, 1H), 7.46 (d, J = 8.0 Hz, 1H), 7.34 (d, J = 1.6 Hz, 1H), 7.29 (d, J = 2.0 Hz, 1H), 3.83-3.82 (m, 1H), 3.48 (s, 2H), 3.31-3.24 (m, 2H), 3.21-3.01 (m, 2H), 2.92 (s, 3H), 2.71-2.56 (m, 5H), 2.40-2.10 (m, 5H), 1.26-1.21 (m, 3H), 1.02-0.97 (m, 1H), 0.55-0.51 (m, 2H), 0.20 (s, 2H). MS (ESI): C₂₆H₃₄ClN₅O₂ requires 483; found 484 [M + H]⁺. |
| E37 | 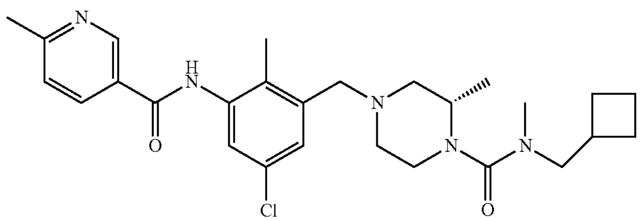 [SMILES: Cc1ccc(C(=O)Nc2cc(Cl)cc(CN3CCN(C(=O)N(C)CC4CCC4)[C@@H](C)C3)c2C)cn1] | DCM/TEA | ¹H NMR (400 MHz, MeOD-d₄): 9.01 (d, J = 2.0 Hz, 1H), 8.28 (dd, J = 8.0 Hz, 3.0 Hz, 1H), 7.48 (d, J = 8.0 Hz, 1H), 7.36 (d, J = 2.0 Hz, 1H), 7.30 (d, J = 2.4 Hz, 1H), 3.82-3.78 (m, 1H), 3.50 (s, 2H), 3.34-3.32 (m, 1H), 3.24-3.21 (m, 2H), 3.18-3.13 (m, 1H), 2.83 (s, 3H), 2.70 (d, J = 12.0 Hz, 1H), 2.64-2.57 (m, 4H), 2.37-2.33 (m, 1H), 2.31 (s, 3H), 2.24-2.17 (m, 1H), 2.10-2.02 (m, 2H), 1.98-1.84 (m, 2H), 1.76-1.67 (m, 2H), 1.26 (d, J = 4.0 Hz, 3H). MS (ESI): C₂₇H₃₆ClN₅O₂ requires 497; found 498 [M + H]⁺. |
| E38 | 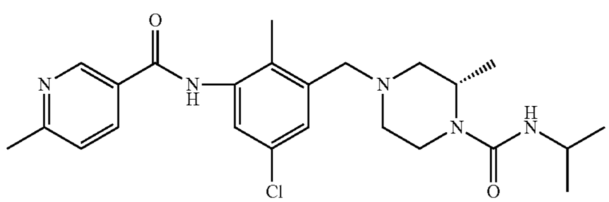 [SMILES: Cc1ccc(C(=O)Nc2cc(Cl)cc(CN3CCN(C(=O)NC(C)C)[C@@H](C)C3)c2C)cn1] | THF/DIPEA | ¹H NMR (400 MHz, MeOD-d₄): 9.02 (s, 1H), 8.28 (dd, J = 8.0 Hz, 4.0 Hz, 1H), 7.47 (d, J = 8.0 Hz, 1H), 7.35 (d, J = 2.0 Hz, 1H), 7.31 (d, J = 2.0 Hz, 1H), 4.18 (brs, 1H), 3.95-3.87 (m, 1H), 3.71 (d, J = 12 Hz, 1H), 3.50 (s, 2H), 3.10-3.03 (m, 1H), 2.80 (d, J = 12.0 Hz, 1H), 2.69 (d, J = 12.0 Hz, 1H), 2.63 (s, 3H), 2.30 (s, 3H), 2.23-2.20 (m, 1H), 2.08-2.01 (m, 1H), 1.22 (d, J = 4.0 Hz, 3H), 1.14 (d, J = 4.0 Hz, 6H). MS (ESI): C₂₄H₃₂ClN₅O₂ requires 457; found 458 [M + H]⁺. |
| E39 | 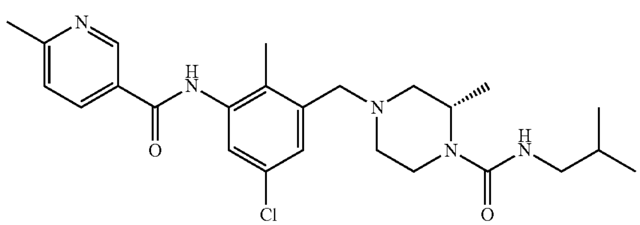 [SMILES: Cc1ccc(C(=O)Nc2cc(Cl)cc(CN3CCN(C(=O)NCC(C)C)[C@@H](C)C3)c2C)cn1] | THF/DIPEA | ¹H NMR (400 MHz, MeOD-d₄): 9.00 (s, 1H), 8.27 (d, J = 8.0 Hz, 1H), 7.47 (d, J = 8.0 Hz, 1H), 7.35 (brs, 1H), 7.30 (brs, 1H), 4.16 (brs, 1H), 3.72 (d, J = 12.0 Hz, 1H), 3.50 (s, 2H), 3.11-2.89 (m, 3H), 2.81 (d, J = 12.0 Hz, 1H), 2.70 (d, J = 12.0 Hz, 1H), 2.63 (brs, 3H), 2.30 (brs, 3H), 2.24-2.21 (m, 1H), 2.08-2.02 (m, 1H), 1.82-1.71 (m, 1H), 1.24-1.21 (m, 3H), 0.90-0.87 (m, 6H). MS (ESI): C₂₅H₃₄ClN₅O₂ requires 471; found 472 [M + H]⁺. |
| E40 | 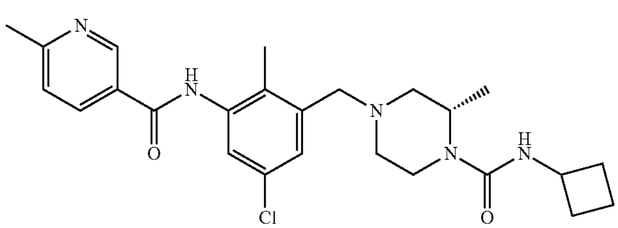 [SMILES: Cc1ccc(C(=O)Nc2cc(Cl)cc(CN3CCN(C(=O)NC4CCC4)[C@@H](C)C3)c2C)cn1] | DCM/DIPEA | ¹H NMR (400 MHz, MeOD-d₄): 9.00 (d, J = 1.6 Hz, 1H), 8.27 (dd, J = 8.4 Hz, 2.4 Hz, 1H), 7.47 (d, J = 8.0 Hz, 1H), 7.35 (d, J = 2.0 Hz, 1H), 7.30 (d, J = 2.0 Hz, 1H), 4.24-4.16 (m, 2H), 3.72 (d, J = 12.4 Hz, 1H), 3.49 (s, 2H), 3.10-3.03 (m, 1H), 2.80 (d, J = 10.8 Hz, 1H), 2.69 (d, J = 11.2 Hz, 1H), 2.63 (s, 3H), 2.30 (s, 3H), 2.28-2.19 (m, 1H), 2.07-1.90 (m, 3H), 1.72-1.60 (m, 2H), 1.21 (d, J = 4.0 Hz, 3H). MS (ESI): C₂₅H₃₂ClN₅O₂ requires 469; found 470 [M + H]⁺. |
| E41 | 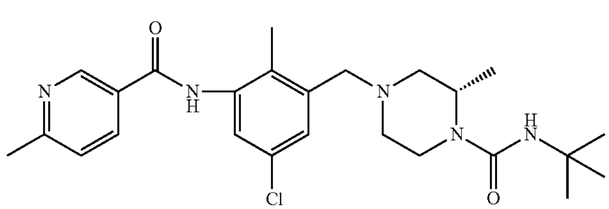 [SMILES: Cc1ccc(C(=O)Nc2cc(Cl)cc(CN3CCN(C(=O)NC(C)(C)C)[C@@H](C)C3)c2C)cn1] | THF/DIPEA | ¹H NMR (400 MHz, DMSO-d₆): 10.12 (s, 1H), 9.02 (s, 1H), 8.21 (d, J = 8.0 Hz, 1H), 7.43 (d, J = 8.4 Hz, 1H), 7.39 (s, 1H), 7.28 (s, 1H), 5.66 (s, 1H), 4.12 (brs, 1H), 3.62 (d, J = 12 Hz, 1H), 3.49-3.41 (m, 2H), 2.87-2.81 (t, J = 12.0 Hz, 1H), 2.69 (d, J = 12.0 Hz, 1H), 2.59-2.56 (m, 4H), 2.20-2.18 (m, 3H), 2.12 (d, J = 8.0 |

| Structure | Solvent/base | Characterization |
|---|---|---|
| E42 | | Hz, 1H), 1.94 (t, J = 12 Hz, 1H), 1.25 (s, 9H), 1.09 (d, J = 4.0 Hz, 3H). MS (ESI): $C_{25}H_{34}ClN_5O_2$ requires 471; found 472 $[M + H]^+$. |
| E42 | DCM/TEA | $^1$H NMR (400 MHz, MeOD-$d_4$): 8.89 (s, 1H), 8.09 (dd, J = 9.6 Hz, 1.2 Hz, 1H), 7.37 (d, J = 2.4 Hz, 1H), 7.32 (d, J = 2.0 Hz, 1H), 4.00-3.98 (m, 1H), 3.51-3.45 (m, 3H), 3.41-3.36 (m, 4H), 3.26-3.23 (m, 1H), 2.76 (d, J = 11.6 Hz, 1H), 2.66-2.62 (m, 4H), 2.32-2.29 (m, 4H), 2.20-2.14 (m, 1H), 1.90-1.82 (m, 4H), 1.30 (d, J = 6.4 Hz, 3H). $^{19}$F NMR (376 MHz, MeOD-$d_4$): −125.43. MS (ESI): $C_{25}H_{31}ClFN_5O_2$ requires 487; found 488 $[M + H]^+$. |
| E43 | DCM/TEA | $^1$H NMR (400 MHz, CDCl$_3$): 8.53 (s, 1H), 7.87 (brs, 2H), 7.67 (s, 1H), 7.16 (d, J = 2.0 Hz, 1H), 4.50-4.45 (m, 1H), 4.06 (brs, 1H), 3.93 (s, 3H), 3.67 (d, J = 12.7 Hz, 1H), 3.46-3.42 (m, 2H), 3.11-3.06 (m, 3H), 2.75 (d, J = 11.1 Hz, 1H), 2.63 (d, J = 11.0 Hz, 1H), 2.55 (s, 3H), 2.30 (s, 3H), 2.25 (dd, J = 11.0 Hz, 3.5 Hz, 1H), 2.09-2.02 (m, 1H), 1.24-1.22 (m, 3H), 0.98-0.95 (m, 1H), 0.51-0.47 (m, 2H), 0.19-0.16 (m, 2H). MS (ESI): $C_{26}H_{34}ClN_5O_3$ requires 499; found 500 $[M + H]^+$. |

Example 44

(S)-cyclopentyl 4-(5-cyano-2-methyl-3-(6-methylnicotinamido)benzyl)-2-methylpiperazine-1-carboxylate (E44)

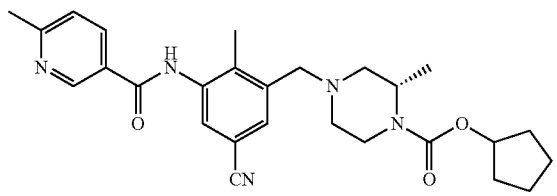 [SMILES: Cc1ccc(C(=O)Nc2cc(C#N)cc(CN3CCN(C(=O)OC4CCCC4)[C@@H](C)C3)c2C)cn1]

To a solution of (S)-N-(5-cyano-2-methyl-3-((3-methylpiperazin-1-yl)methyl)phenyl)-6-methylnicotinamide, 2 hydrochloric acid salt (D70, 40 mg) and TEA (0.014 mL) in THF (10 mL) was added cyclopentyl carbonochloridate (29.7 mg). The mixture was stirred at RT overnight. The mixture was diluted in EA and washed with water for three times. The organic layer was dried with Na$_2$SO$_4$, filtered and concentrated in vacuo. The resulting residue was purified by MADP to afford the title compound (4 mg) as white solid. $^1$H NMR (400 MHz, MeOD-$d_4$): 9.11 (brs, 1H), 8.49 (d, J=7.83 Hz, 1H), 7.87 (brs, 2H), 7.67 (d, J=7.82 Hz, 1H), 5.12 (brs, 2H), 4.69-3.86 (m, 3.5H), 2.91-2.32 (m, 7.5H), 2.11-1.51 (m, 9H), 1.32 (d, J=6.60 Hz, 5H). MS (ESI): $C_{27}H_{33}N_5O_3$, requires 475; found 476 $[M+H]^+$.

Biological Data

As stated above, the compounds according to Formula I are RORγ modulators, and are useful in the treatment of diseases mediated by RORγ. The biological activities of the compounds according to Formula I can be determined using any suitable assay for determining the activity of a candidate compound as a RORγ modulator, as well as tissue and in vivo models.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL motifs in the co-activator SRC1(2) sequences. Short peptide sequences containing the LXXLL motif mimic the behavior of full-length co-activator.

The assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, thus it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in E. coli strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) was fused in frame to residues 263-518 of the human RORγ sequence.

Protein Purification

Approximately 50 g E. coli cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (Invitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mls. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (>8000×)] against PBS [100 mM NaPhosphate, pH 8 and 150 mM NaCl]. The concentration of RORγ-LBD was approximately 30 uM in PBS. Five-fold molar excess of NHS-LC-Biotin (Pierce) was added in a minimal volume of PBS. This solution was incubated with occasional gentle mixing for 60 minutes at ambient RT. The modified RORγ-LBD was dialyzed against 2 buffer changes—TBS pH 8.0 containing 5 mM D17, 2 mM EDTA and 2% sucrose—each at least 20 times of the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five. A biotinylated peptide corresponding to amino acid 676 to 700 (CPSSIISSLTERH-KILHRLLQEGSPS) of the co-activator steroid receptor coactivator SRC1(2) was generated using similar method.

Assay

Preparation of Europium labeled SRC1(2) peptide: biotinylated SRC1(2) solution was prepared by adding an appropriate amount of biotinylated SRC1(2) from the 100 uM stock solution to a buffer containing 10 mM of freshly added DTT from solid to give a filial concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Preparation of APC labeled RORγ-LBD: biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 ul of the reaction mixtures per well was added to the 384-well assay plates containing 1 ul of test compound per well in 100% DMSO. The plates were incubated for 1 hr and then read on ViewLux in Lance mode for EU/APC.

Jurkat Cell Luciferase Assay

RORγ is known to bind to a CNS (conserved non-coding sequences) enhancer element in the IL17 promoter. In this assay, RORγ activity is indirectly assessed using a luciferase reporter construct which contains the human IL17 promoter having the RORγ-specific CNS enhancer element. Inhibition of RORγ activity by a compound will result in a decrease in luciferase activity of Jurkat cells transfected with the reporter construct.

Materials

Jurkat Cell Line

For the luciferase reportor plasmid, the 3 Kb human IL17 promoter containing the RORγ-specific CNS enhancer element was PCR amplified from human genomic DNA and cloned into a pGL4-Luc2/hygro reporter plasmid sequentially as XhoI-HindIII (1.1 Kb) and KpnI-XhoI (1.9 Kb) fragments. For the 1.1 Kb fragment, PCR was used to amplify human IL17 proximal promoter region from genomic DNA of 293T cells using primers as follows: forward primer,5'-CTCGAGTAGAGCAGGACAGGGAGGAA-3' (XhoI site is underlined) and reverse primer, 5'-AAGCTTGGATGGATGAGTTTGTGCCT-3' (HindIII site is underlined). The 1.1 kb DNA bands were excised, purified, and inserted into pMD19-T Simple Vector (Takara). After DNA sequencing confirmation, the 1.1 kb DNA was digested with XhoI and Hindu and inserted into XhoI/HindIII sites of pGL4.31[luc2P/GAL4UAS/Hygro] (Promega) to generate the pIL17-1 kb-luc reporter construct. For the 1.9 Kb fragment, PCR was used to amplify human IL17 promoter region from genomic DNA using primers as follows: forward primer, 5'-GGTACCTGCCCTGCTCTATCCTGAGT-3' (KpnI site is underlined) and reverse primer, 5'-CTCGAGTGGTGAGTGCTGAGAGATGG-3' (XhoI site is underlined). The resulting 1.9 kb DNA bands were excised, gel purified, and cloned into a pMD19-T Simple Vector (Takara). DNA sequencing analysis revealed that there were three point mutations but none of which affected RORγ binding. The 1.9 kb DNA fragment was released by double digestion with KpnI and XhoI and inserted into pIL17-1 kb-luc to generate the luciferase reporter plasmid "pIL17-3 kb-CNS-luc." To overexpress RORγt, the full-length cDNA of human RORγt identical to the published sequence NM_001001523 was cloned into pcDNA3.1 at the KpnI-NotI cloning sites to generate the RORγt overexpression plasmid "CDNA3.1DhRORγ49-8".

The luciferase reporter plasmid and the RORγt overexpression plasmid were transfected into Jurkat cell line and a stable clone was identified. The stable clone was grown in 10% dialyzed FBS in RPMI (1640) with 800 ug/ml geneticin and 400 ug/ml hygromecin.

Assay

Compounds were dissolved in DMSO at three concentrations, 10 mM, 400 uM and 16 uM, and were dispensed into 384-wells assay plate at 40 nl, 12.5 nl, 5 nl respectively. The volume was adjusted with pure DMSO to a give a final uniform volume of 40 nl Jurkat cells described above were counted and centrifuged. The growth medium was discarded and the cells were resuspended with assay medium (phenol red free RPMI) at 1E-6/ml. Cells were added to each of the compounds in the assay plates. Cells were either untreated or treated with CD3 microbeads (Miltenyi Biotec) at 1 ul beads per 500,000 cells. Cells were culture overnight and luciferase assay (Promega) was performed. Data were collected by ViewLux (using luciferase greiner 384 setting).

Th17 Cell Differentiation Assay

ELISA

Mouse CD4+ cells were purified using the CD4+ T Cell Isolation II Kit according to manufacturer's instructions (Miltenyi Biotec). 96 well plates were pre-coated with anti-mCD3 antibody. Un-coated wells were used as controls. CD4+ Cells were resuspended in RPMI 1640 complete medium and were added to the 96-well plates. Cytokine cocktail and the compound were then added to the wells. Antibodies and cytokines (all from R&D Systems) used in the assay were selected from the following: anti-mCD3; anti-mCD28; anti-mIFNγ; anti-mIL4; mIL-6; mIL-23; mIL-1β; hTGF-β1. The culture was incubated at 37° C. for 3 days and supernatants were collected for ELISA. The IL-17 ELISAs were performed according to manufacturer's instructions (R&D Systems). The results were analyzed using Prism software with non-linear regression to determine pIC50.

Intracellular Staining

The Th17 differentiation culture described above was maintained for 5 days and cells were analyzed by IL-17 and IFN-γ intracellular staining according to manufacturer's instructions (BD Biosciences).

Assay Data

The data described below represents a mean pIC50 value of multiple test results if the test was performed more than once. It is understood that the data illustrated below may have reasonable variation depending on the specific conditions and procedures used by the person conducting the testing.

All exemplified compounds except Examples 11, 13, 17, 20, 28 and 44 were tested in the dual FRET assay described above. All tested compounds were found to have a pIC50 between 5 and 8.

All exemplified compounds except Examples 2-16, 18-20, 22, 25, 26-28, 30-33, 35, 36, 38, 42 and 43 were tested in the Jurkat cell luciferase assay described above. All tested compounds were found to have a pIC50 between 6 and 9.

All exemplified compounds except Examples 3, 6, 8-13, 16-19, 26-28, 32, 33 and 38-40 were tested in the Th17 cell differentiation assay described above. All tested compounds were found to have a pIC50 between 6 and 9.

EAE Studies

Experimental Autoimmune Encephalomyelitis (EAE) is an animal model of multiple sclerosis. The ability of a test compound to ameliorate EAE can be measured in the EAE studies. Wild-type mice of the C57BL/6 (B6) strain are maintained under pathogen-free conditions. EAE is induced by intravenous injections of 100 ng of pertussis toxin (List Biological Laboratories) and subcutaneous immunization with an emulsion composed of MOG$_{35-55}$ peptide (300 μg/mouse) in PBS and an equal volume of complete Freund's adjuvant containing 5 mg/ml heat-killed *Mycobacterium tuberculosis* H37Ra (Difco Laboratories) on day 0, followed by another intravenous injections of 100 ng of pertussis toxin on day 2 as described previously (Wang et al. (2006) *J. Clin. Invest.* 116: 2434-2441). For treatment of EAE, each compound or vehicle PBS is given orally from day 0 at various doses selected from 3, 10, 30 and 100 mg/kg twice a day. Mice are scored for disease severity daily using a EAE scoring system (Wang et al. (2006) *J. Clin. Invest.* 116: 2434-2441): 0, no overt signs of disease; 1, limp tail or hind limb weakness but not both; 2, limptail and paraparesis (weakness, incomplete paralysis of one or two hind limbs); 3, paraplegia (complete paralysis of two hind limbs); 4, paraplegia with forelimb weakness or paralysis; and 5, moribund state or death. Clinical score data can be expressed as means±S.E.M.

In Vitro Percutaneous Studies

The in vitro percutaneous study is aimed to predict the level of percutaneous penetration obtained for a compound in a topical formulation for psoriasis. This assay coupled with the intrinsic potency of the compound are used to predict the likelihood of success of a compound to engage the target. The higher the ratio of the percutaneous penetration to the intrinsic potency, the higher the ratio of local skin concentration to the intrinsic potency and therefore the higher the chance of a compound to engage the target in a topical formulation.

The compounds can be manufactured in a modified aqueous cream at pH=6.

Aqueous Cream Composition

| Ingredients | % w/w |
| --- | --- |
| Cetostearyl alcohol | 7.2 |
| Cetomacrogol 1000 | 1.8 |
| White soft paraffin | 15.0 |
| Liquid paraffin | 6.0 |
| Water | 57.0 |
| Na2HPO4 | 0.6 |
| Citric Acid | 0.2 |
| Propylene Glycol | 10.0 |
| Methyl paraben | 0.1 |
| Caffcine | 0.1 |
| API#1 | 1.0 |
| API#2 | 1.0 |
| API#3 | 1.0 |

The study can be conducted with dermatomed abdominal human skin sourced from three skin donors using 2 cm2 Franz diffusion cells. The receiving fluid consisted of Bovine serum albumin (4% w/v) in 0.1% w/v sodium azide in Phospate Buffer Saline and can be heated at 37° C. in order to obtain 32° C. at the skin surface. The cream formulation can be applied on the donor side at a 10 mg dose, i.e. 5 mg/cm$^2$. The samples can be taken at the following time points: t=0, 3, 6, 9 and 24 h. The receiver samples can then be assayed using a method based upon protein precipitation with acetonitrile followed by LC/MS/MS analysis. The percutaneous flux (in ng/cm$^2$/hr) can be determined using the individual API (in a multiple composition) that has permeated into the receiver compartment over 24 hrs per cm$^2$.

Imiquimod-induced Skin Inflammation

Imiquimod is an immune modifying agent that potently activates specific Toll-like receptors TLR7) and Induces irritation/inflammation of the skin that requires the IL23R/RORγ/IL17 axis of the immune system (van der Fits et al, (2009) *J Immunol;* 182:5836-5845; Gray et al, (2013) *Nature Immunol;* June; 14(6):584-92). The imiquimod-induced skin inflammation model can be used to assess the ability of an RORγ inhibitor to reduce Th17-driven inflammation in mice. For the ear-only skin inflammation model in which ear thickness is measured with digital engineer's calipers (Mitutoyo PK-0505), female wild type C57BL/6NTac mice can be obtained from Taconic (Hudson, N.Y.) at 8 to 12 wk of age and given a daily topical dose of 10 mg of commercially available imiquimod cream (5%) (Aldara; Medicis) distributed over both ears at approximately 11:00 h for up to 4 consecutive days. Alternatively, 72 mg of Aldara is distributed over both ears and the shaved/depiliated back skin of mice at approximately 11:00 h for 3 consecutive days to examine RORγ-dependent gene expression (RNA isolated from both ears using Qiazol followed by clean-up on with the RNeasy protocol (Qiagen, Germantown, Md.); Taqman probe/primer sets for B2M (Mm00437762_m1), IL-17A (Mm00439619_m1), IL-17F (Mm00521423_m1), or IL-22 (Mm00444241_m1) (Thermo Fisher Scientific, Inc., Waltham, Mass.) and ex vivo stimulated (anti-CD3 (2 ug/ml, clone eBio500A2, eBioscience, San Diego, Calif.), anti-CD28 (1 ug/ml, clone 37.51, BD Bioscience, San Jose, Calif.), recombinant mouse IL-1β (20 ng/ml, R&D Systems, Minneapolis, Minn.), and recombinant mouse IL-23 (20 ng/ml, R&D Systems, Minneapolis, Minn.) IL-17A protein expression from whole blood (Meso Scale Discovery, Rockville, Md.). For treatment of the skin inflammation in these models, each compound or vehicle (methylcellulose in water, 1% w/v, Sigma Aldrich, St. Louis, Mo.) is administered via oral gavage at approximately 08:00 h and 16:00 h daily at various doses selected from 1, 3, 10, and 30 mg/kg.

Human Peripheral Blood CD4+ T Cell Cultures and Cytokine Analysis

Human biological samples are cryopreserved human CD4+ T cells which may be purchased from AllCells, LLC and/or Stemcell Technologies, Inc. The CD4+ T cells are differentiated to the Th17 subtype by culturing for 5 days in tissue culture plates coated with anti-CD3 antibody (2 µg/mL) in Iscove's modified Dulbecco's medium (IMDM) containing 10% HI-FBS, 55 µM 2-mercaptoethanol and soluble anti-CD28 (3 µg/mL) in the presence of a Th17 skewing cocktail, including IL-1β (10 ng/mL), IL-6 (30 ng/mL), TGFβ (0.5 ng/mL), IL-21 (10 ng/mL), IL-23 (10 ng/mL), anti-IFNγ (10 µg/mL) and anti-IL-4 (10 µg/mL). To examine compound effects on Th17 polarization, freshly thawed CD4+ cells in IMDM supplemented with all Th17 polarization cocktail constituents (above) are seeded at low cell density (20,000 cells/well) directly into anti-CD3 coated round bottom 96-well plates already containing serially diluted compounds. Cells are incubated undisturbed for 5 days at 37° C. Immediately following culture, supernatant is analyzed for secreted IL-17A and IL-22 protein by MSD electrochemiluminescent cytokine assays (Mesoscale Discovery) and ELISA (Quantikine assay, R&D Systems), respectively. Compound treatment(s) may be performed in triplicate.

Methods of Use

The compounds of Formula (I) are modulators of RORγ and can be useful in the treatment of diseases mediated by RORγ, particularly autoimmune or inflammatory diseases. Examples of the inflammatory or autoimmune diseases of the invention include multiple sclerosis, rheumatoid arthritis, psoriasis, ankylosing spondylitis, Crohn's disease, inflammatory bowel disease, Sjorgen's syndrome, optic neuritis, chronic obstructive pulmonary disease, asthma, type I diabetes, neuromyelitis optica, Myasthenia Gavis, uveitis, Guillain-Barre syndrome, psoriatic arthritis, Gaves' disease and allergy. Accordingly, in another aspect the invention is directed to methods of treating autoimmune and inflammatory diseases mediated by RORγ.

In a further aspect, the present invention also provides a compound of Formula (I), or a pharmaceutically acceptable salt or solvate thereof, for use in therapy.

In a further aspect, the present invention also provides a compound of Formula (I), or a pharmaceutically acceptable salt or solvate thereof, for use in the treatment of inflammatory and autoimmune diseases mediated by RORγ.

In a further aspect, the present invention provides a compound of Formula (I), or a pharmaceutically acceptable salt thereof, for use in the treatment of multiple sclerosis.

In a further aspect, the present invention provides a compound of Formula (I), or a pharmaceutically acceptable salt thereof, for use in the treatment of ankylosing spondylitis.

In a further aspect, the present invention is directed to a method of treatment of an inflammatory or autoimmune disease mediated by RORγ, which comprises administering to a human in need thereof, a therapeutically effective amount of a compound of Formula (I), or a pharmaceutically acceptable salt thereof.

In yet a further aspect, the present invention is directed to a method of treating multiple sclerosis, which comprises administering to a human in need thereof, a therapeutically effective amount of a compound of Formula (I), or a pharmaceutically acceptable salt thereof.

In yet a further aspect, the present invention is directed to a method of treating of ankylosing spondylitis, which comprises administering to a human in need thereof, a therapeutically effective amount of a compound of Formula (I), or a pharmaceutically acceptable salt thereof.

In a further aspect, the present invention is directed to the use of a compound of Formula (I), or a pharmaceutically acceptable salt thereof, in the manufacture of a medicament for use in the treatment of an inflammatory or autoimmune disease mediated by RORγ.

In a yet further aspect, the present invention is directed to the use of a compound of Formula (I), or a pharmaceutically acceptable salt thereof, in the manufacture of a medicament for use in the treatment of multiple sclerosis.

In a yet further aspect, the present invention is directed to the use of a compound of Formula (I), or a pharmaceutically acceptable salt thereof, in the manufacture of a medicament for use in the treatment of ankylosing spondylitis.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the human lungs whether inhaled through the mouth or through the nasal passages.

Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the individual being treated, the medical history of the individual to be treated, the nature of concurrent therapy, the desired therapeutic effect, and like factors within the knowledge and expertise of the skilled artisan. It will be further understood by such skilled artisans that suitable dosing regimens may require adjustment given an individual's response to the dosing regimen or over time as individual needs change.

Typical daily dosages may vary depending upon the particular route of administration chosen. Typical daily dosages for oral administration range from 0.1 mg to 1000 mg. Typical daily dosages for topical administration range from about 0.001% to about 10% w/w (weight percent) and preferably from about 0.01% to about 1% w/w.

Additionally, the compounds of the invention may be administered as prodrugs. As used herein, a "prodrug" of a compound of the invention is a functional derivative of the compound which, upon administration to an individual, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to an individual. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the individual such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 0.1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the individual by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the individual from one organ, or portion of the body, to another organ, or portion of the body. Certain pharmaceutically-acceptable excipients may be chosen for their ability to enhance compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

What is claimed is:

1. A compound of Formula I or a pharmaceutically acceptable salt thereof

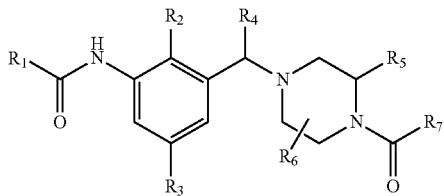

Formula I wherein:
$R_1$ is:
  methyl substituted with i) $C_4$-$C_6$ cycloalkyl optionally substituted with a) one or two F or b) OH; or ii) 5 or 6 membered heterocycloalkyl substituted with C(O)CH$_3$;
  $C_2$-$C_3$ alkyl substituted with CF$_3$ or —SO$_2$CH$_3$;
  6 membered heteroaryl containing 1 or 2 N atom, said heteroaryl is optionally substituted with one to two substituents selected from the group consisting of $C_1$-$C_3$ alkyl, halo, CN and methoxy; or
  phenyl substituted with CN,
$R_2$ is $C_1$-$C_3$ alkyl,
$R_3$ is halo or CN;
$R_4$ is H;
$R_5$ is $C_1$-$C_3$ alkyl;
$R_6$ is H or methyl, and
$R_7$ is selected from the group consisting of:
  4 to 6 membered heterocycloalkyl containing 1 N atom, wherein said heterocycloalkyl is optionally substituted with methyl;
  NRaRb, wherein said Ra is H or methyl, and said Rb is selected from the group consisting of i) methyl substituted with $C_3$-$C_4$ cycloalkyl, ii) $C_4$-$C_5$ cycloalkyl optionally substituted with methyl, and iii) $C_3$-$C_4$ alkyl; and
  ORc, wherein said Rc is i) $C_4$-$C_5$ cycloalkyl; or ii) methyl substituted with $C_3$-$C_4$ cycloalkyl.

2. The compound or salt according to claim 1, wherein $R_1$ is pyridinyl substituted with one or two $C_1$-$C_3$ alkyl.

3. The compound or salt according to claim 1, wherein $R_1$ is pyridinyl substituted with methyl.

4. The compound or salt according to claim 1, wherein $R_1$ is pyridinyl substituted with dimethyl.

5. The compound or salt according to claim 1, wherein $R_1$ is phenyl substituted with CN.

6. The compound or salt according to claim 1, wherein $R_2$ is methyl.

7. The compound or salt according to claim 1, wherein $R_3$ is Cl.

8. The compound or salt according to claim 1, wherein $R_3$ is CN.

9. The compound or salt according to claim 1, wherein $R_4$ is H.

10. The compound or salt according to claim 1, wherein $R_5$ is methyl.

11. The compound or salt according to claim 1, wherein $R_6$ is H.

12. The compound or salt according to claim 1, wherein $R_7$ is pyrrolidinyl.

13. The compound or salt according to claim 1, wherein $R_7$ is piperidinyl.

14. The compound or salt according to claim 1, wherein $R_7$ is ORc, wherein Rc is cyclopentyl.

15. The compound or salt according to claim 1, wherein $R_7$ is NHRb, wherein Rb is methyl substituted with cyclopropyl.

16. The compound or salt according to claim 1, wherein $R_7$ is NHRb, wherein Rb is cyclopentyl.

17. The compound or salt according to claim 1, which is selected from the group consisting of
  (S)-4-(5-chloro-3-(5,6-dimethylnicotinamido)-2-methylbenzyl)-N-(cyclopropylmethyl)-2-methylpiperazine-1-carboxamide;
  (S)-4-(5-chloro-3-(3-cyanobenzamido)-2-methylbenzyl)-N-(cyclopropylmethyl)-2-methylpiperazme-1-carboxamide;
  (S)-N-(5-chloro-2-methyl-3-((3-methyl-4-(pyrrolidine-1-carbony)ppiperazin-1-yl)methyl)phenyl)-3-cyanobenzamide;
  (S)-4-(5-chloro-2-methyl-3-(6-methylnicotinamido)benzyl)-N-cyclopentyl-2-methylpiperazine-1-carboxamide;
  (S)-N-(5-chloro-2-methyl-3((3-methyl-4-(piperidine-1-carbonyl)piperazin-1-yl)methyl)phenyl)-6-methylnicotinamide, and
  (S)-cyclopentyl 4-(5-cyano-2-methyl-3-(6-methylnicotinamido)benzyl)-2-methylpiperazine-1-carboxylate.

18. A pharmaceutical composition which comprises a compound or a pharmaceutically acceptable salt thereof according to claim 1 and a pharmaceutically acceptable carrier or excipient.

19. A method of treating psoriasis comprising administering to a human in need thereof an effective amount of a compound or a pharmaceutically acceptable salt according to claim 1.

20. A method of treating ankylosing spondylitis comprising administering to a human in need thereof an effective amount of a compound or a pharmaceutically acceptable salt according to claim 1.

21. A method of treating multiple sclerosis comprising administering to a human in need thereof an effective amount of a compound or a pharmaceutically acceptable salt according to claim 1.

* * * * *